(12) United States Patent
Sun et al.

(10) Patent No.: US 7,709,647 B2
(45) Date of Patent: May 4, 2010

(54) TETRAHYDROQUINOLINE CANNABINOID RECEPTOR MODULATORS

(75) Inventors: Chongqing Sun, East Windsor, NJ (US); William R. Ewing, Yardley, PA (US); Yanting Huang, Pennington, NJ (US); Annapurna Pendri, Glastonbury, CT (US); Samuel Gerritz, Guilford, CT (US); Bruce A. Ellsworth, Princeton, NJ (US); Natesan Murugesan, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/104,553

(22) Filed: Apr. 17, 2008

(65) Prior Publication Data
US 2008/0200459 A1    Aug. 21, 2008

Related U.S. Application Data

(63) Continuation of application No. 11/334,204, filed on Jan. 18, 2006, now abandoned.

(60) Provisional application No. 60/644,644, filed on Jan. 18, 2005.

(51) Int. Cl.
C07D 215/38     (2006.01)
A61K 31/4709   (2006.01)

(52) U.S. Cl. .................................. 546/159; 514/313

(58) Field of Classification Search .................. 514/313; 546/159
See application file for complete search history.

(56) References Cited

U.S. PATENT DOCUMENTS

| | | | |
|---|---|---|---|
| 3,674,836 | A | 7/1972 | Creger |
| 3,983,140 | A | 9/1976 | Endo et al. |
| 4,027,009 | A | 5/1977 | Grier et al. |
| 4,231,938 | A | 11/1980 | Monaghan et al. |
| 4,346,227 | A | 8/1982 | Terahara et al. |
| 4,379,785 | A | 4/1983 | Weyer et al. |
| 4,448,784 | A | 5/1984 | Glamkowski et al. |
| 4,450,171 | A | 5/1984 | Hoffman et al. |
| 4,499,289 | A | 2/1985 | Baran et al. |
| 4,613,610 | A | 9/1986 | Wareing |
| 4,639,436 | A | 1/1987 | Junge et al. |
| 4,647,576 | A | 3/1987 | Hoefle et al. |
| 4,681,893 | A | 7/1987 | Roth |
| 4,686,237 | A | 8/1987 | Anderson |
| 4,759,923 | A | 7/1988 | Buntin et al. |
| 4,871,721 | A | 10/1989 | Biller |
| 4,904,769 | A | 2/1990 | Rauenbusch |
| 4,924,024 | A | 5/1990 | Biller |
| 5,006,530 | A | 4/1991 | Angerbauer et al. |
| 5,011,930 | A | 4/1991 | Fujikawa et al. |
| 5,177,080 | A | 1/1993 | Angerbauer et al. |
| 5,260,440 | A | 11/1993 | Hirai et al. |
| 5,273,995 | A | 12/1993 | Roth |
| 5,354,772 | A | 10/1994 | Kathawala |
| 5,385,929 | A | 1/1995 | Bjorge et al. |
| 5,447,954 | A | 9/1995 | Gribble et al. |
| 5,488,064 | A | 1/1996 | Sher |
| 5,491,134 | A | 2/1996 | Sher et al. |
| 5,506,219 | A | 4/1996 | Robl |
| 5,541,204 | A | 7/1996 | Sher et al. |
| 5,594,016 | A | 1/1997 | Ueno et al. |
| 5,612,359 | A | 3/1997 | Murugesan |
| 5,686,104 | A | 11/1997 | Mills et al. |
| 5,691,322 | A | 11/1997 | Robl |
| 5,698,527 | A | 12/1997 | Kim |
| 5,712,396 | A | 1/1998 | Magnin et al. |
| 5,753,675 | A | 5/1998 | Wattanasin |
| 5,770,615 | A | 6/1998 | Cheng et al. |
| 5,776,983 | A | 7/1998 | Washburn et al. |
| 5,990,109 | A | 11/1999 | Chen et al. |
| 6,017,919 | A | 1/2000 | Inaba et al. |
| 6,043,265 | A | 3/2000 | Murugesan et al. |
| 6,184,231 | B1 | 2/2001 | Hewawasam et al. |
| 6,387,926 | B1 | 5/2002 | Bhide et al. |
| 6,414,002 | B1 | 7/2002 | Cheng et al. |
| 6,635,626 | B1 | 10/2003 | Barrish et al. |

(Continued)

FOREIGN PATENT DOCUMENTS

EP    0 142 146    5/1985

(Continued)

OTHER PUBLICATIONS

Biller, S. et al., "Squalene Synthase Inhibitors", Current Pharmaceutical Design, vol. 2, pp. 1-40 (1996).

(Continued)

*Primary Examiner*—Rita J Desai
*Assistant Examiner*—David K O'Dell
(74) *Attorney, Agent, or Firm*—Maureen S. Gibbons; Burton Rodney

(57) ABSTRACT

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents. The compounds have the general Formula I:

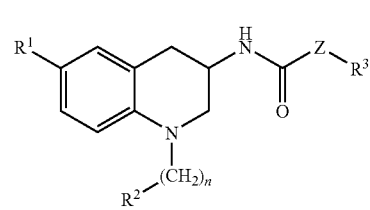

including all prodrugs, pharmaceutically acceptable salts and stereoisomers, $R^1$, $R^2$, $R^3$, n, and Z are described herein.

2 Claims, No Drawings

U.S. PATENT DOCUMENTS

| | | | |
|---|---|---|---|
| 6,956,033 | B2 | 10/2005 | Ogawa et al. |
| 7,361,766 | B2 * | 4/2008 | Sun et al. .................... 546/122 |
| 2004/0171613 | A1 | 9/2004 | Iwamura et al. |
| 2005/0014786 | A1 | 1/2005 | Sun et al. |
| 2005/0222138 | A1 | 10/2005 | Ohhata et al. |
| 2006/0128689 | A1 * | 6/2006 | Gomtsyan et al. ...... 514/217.01 |
| 2006/0154956 | A1 | 7/2006 | Sun et al. |
| 2006/0160850 | A1 | 7/2006 | Sun et al. |

FOREIGN PATENT DOCUMENTS

| | | |
|---|---|---|
| EP | 0 221 025 | 5/1987 |
| EP | 0 675 714 81 | 10/1995 |
| EP | 0 818 448 B1 | 1/1998 |
| EP | 0 992 496 B1 | 4/2000 |
| EP | 1 022 272 B1 | 7/2000 |
| FR | 2 596 393 | 10/1987 |
| GB | 2 205 837 | 12/1988 |
| GB | 2 304 106 | 3/1997 |
| GR | DE 196 22 222 A1 | 12/1997 |
| WO | WO 86/03488 | 6/1986 |
| WO | WO 86/07054 | 12/1986 |
| WO | WO 94/15592 | 7/1994 |
| WO | WO 97/21993 | 6/1997 |
| WO | WO 97/35576 | 10/1997 |
| WO | WO 97/48701 | 12/1997 |
| WO | WO 99/00353 | 1/1999 |
| WO | WO 00/01389 | 1/2000 |
| WO | WO 00/15201 | 3/2000 |
| WO | WO 00/30665 | 6/2000 |
| WO | WO 00/38722 | 7/2000 |
| WO | WO 00/50574 | 8/2000 |

OTHER PUBLICATIONS

Biller, S. et al., "Isoprenoid (Phosphinylmethyl) phosphonates as Inhibitors of Squalene Synthetase", J. of Medicinal Chemistry, vol. 31(10), pp. 1869-1871 (1988).

Corey, E. et al., "Application of Unreactive Analogs of Terpenoid Pyrophosphates to Studies of Multistep Biosynthesis. Demonstration that "Presqualene Pyrophosphate" is an Essential Intermediate on the Path to Squalene", J A C S, vol. 98(5), pp. 1292-1293 (1976).

Colombo, G. et al., "Appetite Suppression and Weight Loss after the Cannabinoid Antagonist SR 141716", Life Sciences, vol. 63(8), pp. PL-113-117 (1998).

Davidsen, S. et al., "N-(Acyloxyalkyl) pyridinium Salts as Soluble Prodrugs of a Potent Platelet Activating Factor Antagonist", J. of Medicinal Chemistry, vol. 37(26), pp. 4423-4429 (1994).

DiMarzo, V. et. al., "Leptin-regulated endocannabinoids are involved in maintaining food intake", Nature, vol. 410, pp. 822-825 (2001).

Ettmayer, P. et al., "Lessons Learned from Marketed and Investigational Prodrugs", J. of Medicinal Chemistry, vol. 47(10), pp. 2393-2404 (2004).

Galiegue, S. et al., "Expression of central and peripheral cannabinoid receptors in human immune tissues and leukocyte subpopulations", Eur. J. Biochem., vol. 232, pp. 54-61 (1995).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16(1), pp. 16-30 (1998).

Glass, M. et al., "Cannabinoid Receptors in the Human Brain: A Detailed Anatomical and Quantitative Autoradiographic Study in the Fetal, Neonatal and Adult Human Brain", Neuroscience, vol. 77(2), pp. 299-318 (1997).

Hara, S., "Ileal Na+/bile acid cotransporter inhibitors", Drugs of the Future, vol. 24(4), pp. 425-430 (1999).

Hildebrandt, A. et al., "Antiobesity effects of chronic cannabinoid $CB_1$ receptor antagonist treatment in diet-induced obese mice", European J. of Pharmacology, vol. 462, pp. 125-132 (2003).

Hollenbaugh, D. et al., "The human T cell antigen gp39, a member of the TNF gene family, is a ligand for the CD40 receptor: expression of a soluble form of gp39 with B cell co-stimulatory activity", The EMBO Journal, vol. 11(12), pp. 4313-4321 (1992).

Hollenbaugh, D. et al., "Cleavable CD40lg fusion proteins and the binding to sgp39", J. of Immunological Methods, vol. 188, pp. 1-7 (1995).

Krause, B. et al., "ACAT Inhibitors: Physiologic Mechanisms for Hypolipidemic and Anti-Atherosclerotic Activities in Experimental Animals", Inflammation: Mediators and Pathways, pp. 173-198 (1995).

Ljung, B. et al., "AZ 242, a novel PPARα/γ agonist with beneficial effects on insulin resistance and carbohydrate and lipid metabolism in ob/ob mice and obese Zucker rats", J. of Lipid Research, vol. 43, pp. 1855-1863 (2002).

Matsuda, L. et al., "Structure of a cannabinoid receptor and functional expression of the cloned cDNA", Nature, vol. 346, pp. 561-563 (1990).

McClard, R. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Moreland, L. et al., "Treatment of Rheumatoid Arthritis with a recombinant human tumor necrosis factor receptor (p75)-Fc Fusion Protein", The New England J. of Medicine, vol. 337(3), pp. 141-147 (1997).

Munro, S. et al., "Molecular characterization of a peripheral receptor for cannabinoids", Nature, vol. 365, pp. 61-65 (1993).

Nicolosi, R. et al., "The ACAT inhibitor, CI-1011 is effective in the prevention and regression of aortic fatty streak area in hamsters", Atherosclerosis, vol. 137, pp. 77-85 (1998).

Ortiz de Montellano, P. et al., "Inhibition of Squalene Synthetase by Farnesyl Pyrophosphate Analogues$^1$" J. of Medicinal Chem., vol. 20(2), pp. 243-249 (1977).

Rosenblum, S. et al., "Discovery of 1-(4-Fluorophenyl)-(3-R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, pp. 973-980 (1998).

Salisbury, B. et al., "Hypocholesterolemic activity of a novel inhibitor of cholesterol absorption, SCH 48461", Atherosclerosis, vol. 115, pp. 45-63 (1995).

Sliskovic, D. et al., "ACAT Inhibitors: Potential Anti-atherosclerotic Agents", Current Medicinal Chemistry, vol. 1, pp. 204-225 (1994).

Sorbera, L. et al., "Avasimibe. Treatment of Lipoprotein Disorders ACAT Inhibitor", Drugs of the Future, vol. 24(1), pp. 9-15 (1999).

Stout, D., "Inhibitors of Acyl-CoA: Cholesterol O-Acyl Transferase (ACAT) as Hypocholesterolemic Agents. 6. The First Water-Soluble ACAT Inhibitor with Lipid-Regulating Activity. Inhibitors of Acyl-CoA: Cholesterol Acyltransferase (ACAT).7. Development of a Series of Substituted N-Phenyl-N-[(1-phenylcyclopentyl)-methyl]ureas with enhanced Hypocholestrolemic Activity", Chemtracts-Organic Chemistry, vol. 8, pp. 359-362 (1995).

Rowland, N. et al., "Effects of the cannabinoid receptor antagonist SR 141716, alone and in combination with dexfenfluramine or naloxone, on food intake in rats", Psychopharmacology, vol. 159, pp. 111-116 (2001).

Smith, C. et al. "RP 73163: A Bioavailable Alkylsulphinyl-Diphenylimidazole ACAT Inhibitor", Bioorganic & Medicinal Chemistry Letters, vol. 6(1), pp. 47-50 (1996).

Trillou, C. et al., "Anti-obesity effect of SR141716, a CB1 receptor antagonist, in diet-induced obese mice", Am. J. Physiol Regul Integr Comp. Physiol., vol. 284, pp. R345-R353 (2003).

Williams, C. et al., "Anandamide induces overeating: mediation by central cannabinoid (CB1) receptors", Psychopharmacology, vol. 143, pp. 315-137 (1999).

Yajima, K. et al., "Combination therapy with PPARγ and PPARα agonists increases glucose-stimulated insulin secretion in db/db mice", Am. J. Physiol Endocrinol Metab., vol. 284, pp. E966-E971 (2003).

Reggio, "Endocannabinoid Structure-Activity Relationships for Interaction at the Cannabinoid Receptors", Prostaglandins, Leukotrienes and Essential Fatty Acids, vol. 66, pp. 143-160, 2002.

Padgett, "Recent Developments in Cannabinoid Ligands", Life Sciences, vol. 77, pp. 1767-1798, 2005.

Stern et al., "Novel-4-Oxo-1,4-dihydroquinoline-3-carboxamide Derivatives as New CB2 Cannabinoid Receptors Agonists: Synthesis, Pharmacological Properties and Molecular Modeling", Journal of Medicinal Chemistry, vol. 49, pp. 70-79, 2006.

Martin et al. "Do Structurally Similar Molecules Have Similar Biological Activity?", Journal of Medicinal Chemistry, vol. 45, pp. 4350-4358, 2002.

Kenakin et al., "The Ligand Paradox Between Affinity and Efficacy: Can You Be There and Not Make a Difference?", Trends in Pharmacological Sciences, vol. 23, pp. 275-280, 2002.

Kenakin, "Principles: Receptor Theory in Pharmacology", Trends in Pharmacological Sciences, vol. 25, pp. 186-192, 2004.

Memorandum to: Members and Consultants, Endocrinologic & Metabolic Drugs Advisory Committee From: Division of Metabolism and Endocrinology Products (DMEP) Office of Drug Evaluation II Center for Drug Evaluation & Research, Food and Drug Administration: Date: May 22, 2007.

Database Caplus: Chemical Abstracts XP002384250, Database accession No. 1995:358755, registry Nos. 160974-25-4 and abstract & JP 06 263736 A (Takeda Chemical Industries Ltd. Japan) Sep. 20, 1994.

* cited by examiner

TETRAHYDROQUINOLINE CANNABINOID RECEPTOR MODULATORS

CROSS-REFERENCE TO RELATED APPLICATIONS

This application is a continuation of U.S. Ser. No. 11/334,204 filed Jan. 18, 2006 which claims priority to U.S. Provisional Application No. 60/644,644, filed Jan. 18, 2005, the contents of which are herein incorporated by reference in their entirety.

BACKGROUND

Delta-9-tetrahydrocannabinol or Delta-9 THC, the principle active component of Cannabis sativa (marijuana), is a member of a large family of lipophilic compounds (i.e., cannabinoids) that mediate physiological and psychotropic effects including regulation of appetite, immunosuppression, analgesia, inflammation, emesis, anti-nocioception, sedation, and intraocular pressure. Other members of the cannabinoid family include the endogenous (arachidonic acid-derived) ligands, anandamide, 2-arachidonyl glycerol, and 2-arachidonyl glycerol ether. Cannabinoids work through selective binding to and activation of C-protein coupled cannabinoid receptors. Two types of cannabinoid receptors have been cloned including CB-1 (L. A. Matsuda, et al., *Nature*, 346, 561-564 (1990)), and CB-2 (Munro, S. et al., *Nature*, 365:61-65 (1993)). The CB-1 receptor is highly expressed in the central and peripheral nervous systems (Glass, M. et al., *Neuroscience*, 77:299-318 (1997)), while the CB-2 receptor is highly expressed in immune tissue, particularly in spleen and tonsils. The CB-2 receptor is also expressed on other immune system cells, such as lymphoid cells (Galiegue, S. et al., *Eur. J. Biochem.*, 232:54-61 (1995)). Agonist activation of cannabinoid receptors results in inhibition of cAMP accumulation, stimulation of MAP kinase activity, and closure of calcium channels.

There exists substantial evidence that cannabinoids regulate appetitive behavior. Stimulation of CB-1 activity by anandamide or Delta-9 THC results in increased food intake and weight gain in multiple species including humans (Williams et al., *Psychopharm.*, 143:315-317 (1999)). Genetic knock-out of CB-1 result in mice that were hypophagic and lean relative to wild-type litter mates (DiMarzo et al., *Nature*, 410:822-825 (2001)). Published studies with CB-1 small molecule antagonists have demonstrated decreased food intake and body weight in rats (Trillou et al., *Am. J. Physiol. Regul. Integr. Comp. Physiol.*, R345-R353 (2003)). Chronic administration of the CB-1 antagonist AM-251 for two weeks resulted in substantial body weight reduction and decreased adipose tissue mass (Hildebrandt et al., *Eur. J. Pharm.*, 462: 125-132 (2003)). There are multiple studies that have assessed the anorexic effect of the Sanofi CB-1 antagonist, SR-141716 (Rowland et al., *Psychopharm.*, 159:111-116 (2001); Colombo et al., *Life Sci.*, 63:113-117 (1998)). There are at least two CB-1 antagonists in clinical trials for regulation of appetite, Sanofi's SR-141716 and Solvay's SLV-319. Published Phase IIb data reveal that SR-141716 dose-dependently reduced body weight in human subjects over a 16 week trial period. CB-1 antagonists have also been shown to promote cessation of smoking behavior. Phase II clinical data on smoking cessation were presented in September of 2002 at Sanofi-Synthelabo's Information meeting. This data showed that 30.2% of patients treated with the highest dose of SR-141716 stayed abstinent from cigarette smoke relative to 14.8% for placebo.

DETAILED DESCRIPTION

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents. The compounds have the general Formula I:

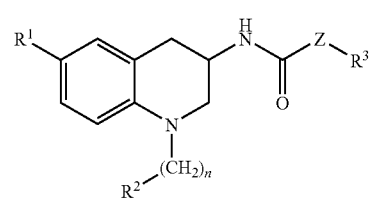

I including all prodrugs, pharmaceutically acceptable salts and stereoisomers, $R^1$, $R^2$, $R^3$, n, and Z are described herein.

DEFINITIONS

The following definitions apply to the terms as used throughout this specification, unless otherwise limited in specific instances.

As used herein, the term "alkyl" denotes branched or unbranched hydrocarbon chains containing 1 to 20 carbons, preferably 1 to 12 carbons, and more preferably 1 to 8 carbons, in the normal chain, such as, methyl, ethyl, propyl, isopropyl, butyl, sec-butyl, iso-butyl, tert-butyl, pentyl, hexyl, isohexyl, heptyl, 4,4-dimethylpentyl, octyl, 2,2,4-trimethylpentyl and the like. Further, alkyl groups, as defined herein, may optionally be substituted on any available carbon atom with one or more functional groups commonly attached to such chains, such as, but not limited to hydroxyl, halo, haloalkyl, mercapto or thio, cyano, alkylthio, cycloalkyl, heterocyclyl, aryl, heteroaryl, carboxyl, carbalkoyl, carboxamido, carbonyl, alkenyl, alkynyl, nitro, amino, alkoxy, aryloxy, arylalkyloxy, heteroaryloxy, amido, —OPO₃H, —OSO₃H, and the like to form alkyl groups such as trifluoromethyl, 3-hydroxyhexyl, 2-carboxypropyl, 2-fluoroethyl, carboxymethyl, cyanobutyl and the like.

Unless otherwise indicated, the term "alkenyl" as used herein by itself or as part of another group refers to straight or branched chains of 2 to 20 carbons, preferably 2 to 12 carbons, and more preferably 2 to 8 carbons with one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Further, alkenyl groups, as defined herein, may optionally be substituted on any available carbon atom with one or more functional groups commonly attached to such chains, such as, but not limited to halo, haloalkyl, alkyl, alkoxy, alkynyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "alkynyl" as used herein by itself or as part of another group refers to straight or branched chains of 2 to 20 carbons, preferably 2 to 12 carbons and more preferably 2 to 8 carbons with one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Further, alkynyl groups, as defined herein, may optionally be substituted on any available carbon atom with one or more functional groups commonly attached to such chains, such as, but not limited to halo, haloalkyl, alkyl, alkoxy, alkenyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the alkyl substituents set out herein Unless otherwise indicated, the term "cycloalkyl" as employed herein alone or as part of another group includes saturated or partially unsaturated (containing one or more double bonds) cyclic hydrocarbon groups containing 1 to 3 rings, appended or fused, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

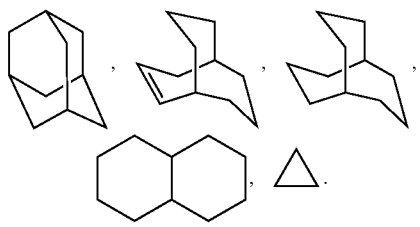

Further, any cycloalkyl may be optionally substituted through any available carbon atoms with one or more groups selected from hydrogen, halo, haloalkyl, alkyl, alkoxy, haloalkyloxy, hydroxyl, alkenyl, alkynyl, aryl, aryloxy, heteroaryl, heteroaryloxy, arylalkyl, heteroarylalkyl, alkylamido, alkanoylamino, oxo, acyl, arylcarbonylamino, amino, nitro, cyano, thiol and/or alkylthio and/or any of the alkyl substituents.

The term "cycloalkylalkyl" as used herein alone or as part of another group refers to alkyl groups as defined above having a cycloalkyl substituent, wherein said "cycloalkyl" and/or "alkyl" groups may optionally be substituted as defined above.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, for example

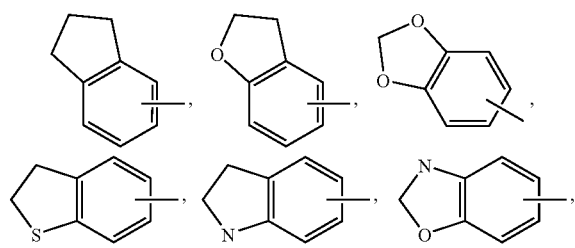

-continued

Further, "aryl", as defined herein, may optionally be substituted with one or more functional groups, such as halo, alkyl, haloalkyl, alkoxy, haloalkoxy, alkenyl, alkynyl, cycloalkyl, cycloalkylalkyl, heterocyclyl, heterocycloalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxyl, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. et al., eds., *Comprehensive Heterocyclic Chemistry: The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature 1982-1995*, Elsevier Science, Inc., Tarrytown, N.Y. (1996); and references therein. Further, "heteroaryl", as defined herein, may optionally be substituted with one or more substituents such as the substituents included above in the definition of "substituted alkyl" and "substituted aryl". Examples of heteroaryl groups include the following:

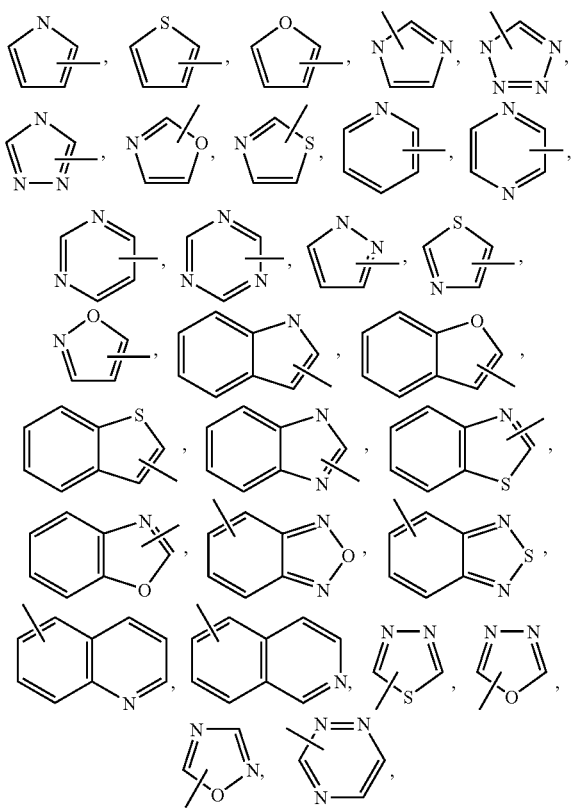

and the like.

The term "heteroarylalkyl" as used herein alone or as part of another group refers to alkyl groups as defined above having a heteroaryl substituent, wherein said heteroaryl and/or alkyl groups may optionally be substituted as defined above.

The term "heterocyclo", "heterocycle", "heterocyclyl" or "heterocyclic ring", as used herein, represents an unsubstituted or substituted stable 4 to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. et al., eds., *Comprehensive Heterocyclic Chemistry The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature* 1982-1995, Elsevier Science, Inc., Tarrytown, N.Y. (1996); and references therein.

The term "heterocycloalkyl" as used herein alone or as part of another group refers to alkyl groups as defined above having a heterocyclyl substituent, wherein said heterocyclyl and/or alkyl groups may optionally be substituted as defined above.

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like.

The term "alkoxy", "aryloxy", "heteroaryloxy", "arylalkyloxy", or "heteroarylalkyloxy" as employed herein alone or as part of another group includes an alkyl or aryl group as defined above linked through an oxygen atom.

The term "halogen" or "halo" as used herein alone or as part of another group refers to chlorine, bromine, fluorine, and iodine, with bromine, chlorine or fluorine being preferred.

The term "cyano," as used herein, refers to a —CN group.

The term "methylene," as used herein, refers to a $CH_2$— group.

The term "nitro," as used herein, refers to a —$NO_2$ group.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate, nitrate or acetate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "bioactive metabolite" as employed herein refers to any functional group contained in a compound of formula I with an open valence for further substitution wherein such substitution can, upon biotransformation, generate a compound of formula I. Examples of such functional groups of bioactive metabolites include, but are not limited to, —OH, —NH or functional groups wherein the hydrogen can be replaced with a functional group such as —$PO_3H_2$ for example, which, upon biotransformation generates an —OH or —NH functional group of a compound of formula I.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. Prodrug esters may also include-but are not limited to groups such as phosphate esters, phosphonate esters, phosphonamidate esters, sulfate esters, sulfonate esters, and sulfonamidate esters wherein the ester may be further substituted with groups that confer a pharmaceutical advantage such as-but not limited to-favorable aqueous solubility or in vivo exposure to the bioactive component formula I.

The term "prodrug" as employed herein includes functionalization of bioactive amine- or hydroxyl-containing compounds of formula I to form alkyl-, acyl-, sulfonyl-, phosphoryl-, or carbohydrate-substituted derivatives. Such derivatives are formed by reacting compounds of formula I with alkylating-, acylating-, sulfonylating-, or phosphorylating reagents employing procedures known to those skilled in the art. Alkylation of amines of formula I may result in-but are not limited to-derivatives that include spacer units to other prodrug moieties such as substituted alkyoxymethyl-, acyloxymethyl-, phosphoryloxymethyl-, or sulfonyloxymethyl-groups. Alkylation of amines of formula I may result in the generation of quanternary amine salts that act in vivo to provide the bioactive agent (i.e., the compound of formula I).

Preferred prodrugs consist of a compound of formula I where a pendant hydroxyl is phosphorylated to generate a phosphate derivative. Such a prodrug may also include a spacer group between the compound of formula I and the phosphate group, such as a methylenoxy-group. Methods to generate such a prodrug from a compound of formula I are known to those skilled in the art, and are listed in the references below.

Preferred prodrugs also consist of a compound of formula I where a pendant amine, such as a pyridine group, is alkylated with a group, such as methyl, to form a quanternary ammonium ion salt. Methods to generate such a prodrug from a compound of formula I are known to those skilled in the art, and are listed in the references below.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

a) *The Practice of Medicinal Chemistry*, Camille G. Wermuth et al., Ch. 31 (Academic Press, 1996);
b) *Design of prodrugs*, edited by H. Bundgaard (Elsevier, 1985);
c) *A Textbook of Drug Design and Development*, P. Krogsgaard-Larson and H. Bundgaard, eds. Ch. 5, pp. 113-191 (Harwood Academic Publishers, 1991);
d) *Hydrolysis in Drug and Prodrug Metabolism*, B. Testa and J. M. Mayer, (Verlag Helvetica Chimica Acta AG, Zurich, Switzerland; Wiley-VCH, Weinheim, Federal Republic of Germany, 2003);
e) Ettmayer, P. et al., "Lessons Learned from Marketed and Investigational Prodrugs", *J. Med. Chem.*, 47(10):2393-2404 (2004); and
f) Davidsen, S. K. et al. "N-(Acyloxyalkyl)pyridinium Salts as Soluble Prodrugs of a Potent Platelet Activating Factor Antagonist" *J. Med. Chem.*, 37(26)-4423-4429 (1994).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration.

All stereoisomers of the compounds of the instant invention are contemplated, either in mixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When racemic or diastereomeric products are prepared, they can be separated by conventional methods for example, chromatographic techniques, chiral HPLC or fractional crystallization.

The compounds of formula I of the invention can be prepared as shown in the following reaction schemes and description thereof, as well as relevant published literature procedures that may be used by one skilled in the art. Exemplary reagents and procedures for these reactions appear hereinafter and in the working Examples.

ABBREVIATIONS

The following abbreviations are employed in the Schemes, Examples and elsewhere herein:

AcOH=acetic acid

Boc=tert-butoxycarbonyl

Cbz=benzyloxycarbonyl

DCE=1,2-dichloroethane

DIPEA=N,N-diisopropylethylamine

DMF=N,N-dimethylformamide

EDAC=1-(3-dimethylaminopropyl)-3-ethylcarbodiimide hydrochloride

EtOAc=ethyl acetate $Et_3N$=triethylamine $Et_2O$=diethyl ether

HOBt=1-hydroxybenzotriazole hydrate

HPLC or LC=high performance liquid chromatography

LAH=lithium aluminum hydride

MeOH=methanol

MS or Mass Spec=mass spectrometry

NaCl=sodium chloride $NaHCO_3$=sodium bicarbonate $NaBH(OAc)_3$=sodium triacetoxyborohydride $Na_2SO_4$=sodium sulfate NaOH=sodium hydroxide NMM=4-methylmorpholine OTf trifluoromethanesulfonyl PG=protecting group PXPd=dichloro-bis(chloro-di-tert-butylphosphine)palladium RT=room temperature TFA=trifluoroacetic acid THF=tetrahydrofuran min=minute(s)

h=hour(s)

L=liter mL milliliter

μL=microliter g=gram(s)

mg=milligram(s)

mol=moles mmol=millimole(s)

nM=nanomolar

Compounds of the present invention may be prepared by procedures illustrated in the accompanying schemes.

Methods of Preparation

The compounds of the present invention may be prepared by methods such as those illustrated in the following Scheme 1 to 6. Solvents, temperatures, pressures, and other reaction conditions may readily be selected by one of ordinary skill in the art. Starting materials are commercially available or can be readily prepared by one of ordinary skill in the art using known methods. For all of the schemes and compounds described below, $R^1$, $R^2$, $R^3$, n, and Z are as described for a compound of formula I.

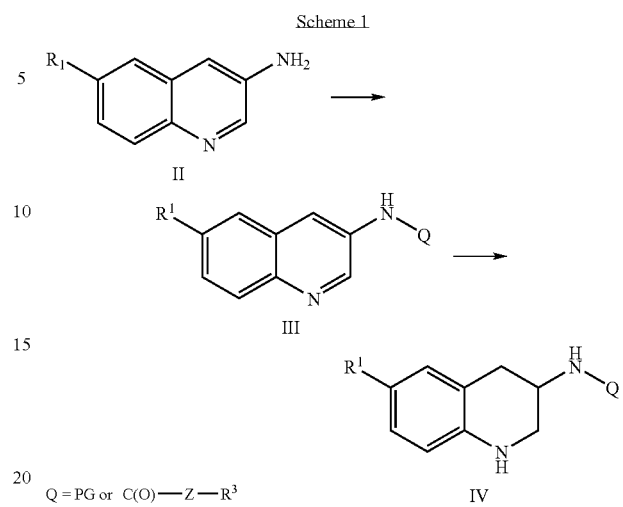

As illustrated in Scheme 1, the amino group of compound II can be suitably protected by, for example, a tert-butyloxycarbonyl, or an acyl group as shown in III. Compound II can be obtained commercially, or can be readily prepared by one skilled in the art. Reduction of III via catalytic hydrogenation in the presence of a transition metal catalyst, such as platinum oxide, or palladium hydroxide on carbon provides intermediate IV.

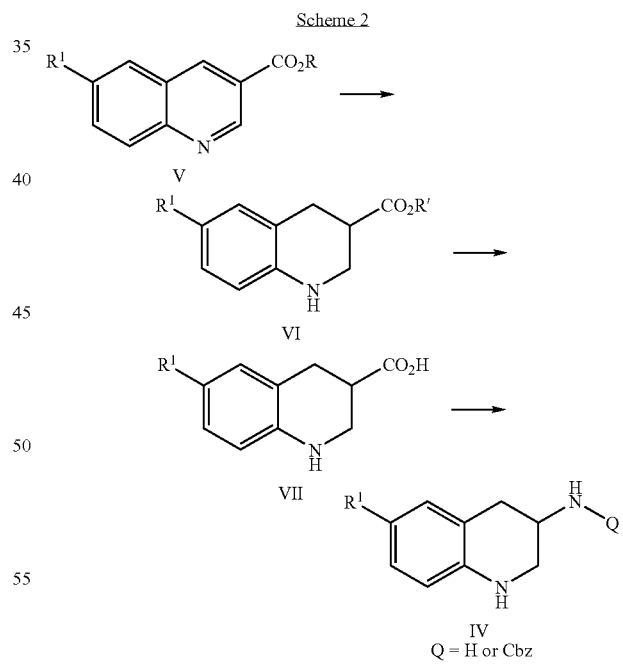

As illustrated in Scheme 2, compound V can be reduced via catalytic hydrogenation in the presence of a transition metal catalyst, such as platinum oxide, or palladium hydroxide on carbon to provide intermediate VI, which can be hydrolyzed to provide acid VII. Conversion of the carboxylic acid of VII via Curtius rearrangement reaction affords IV as either free or protected amine. Compound V can be obtained commercially, or can be readily prepared by one skilled in the art.

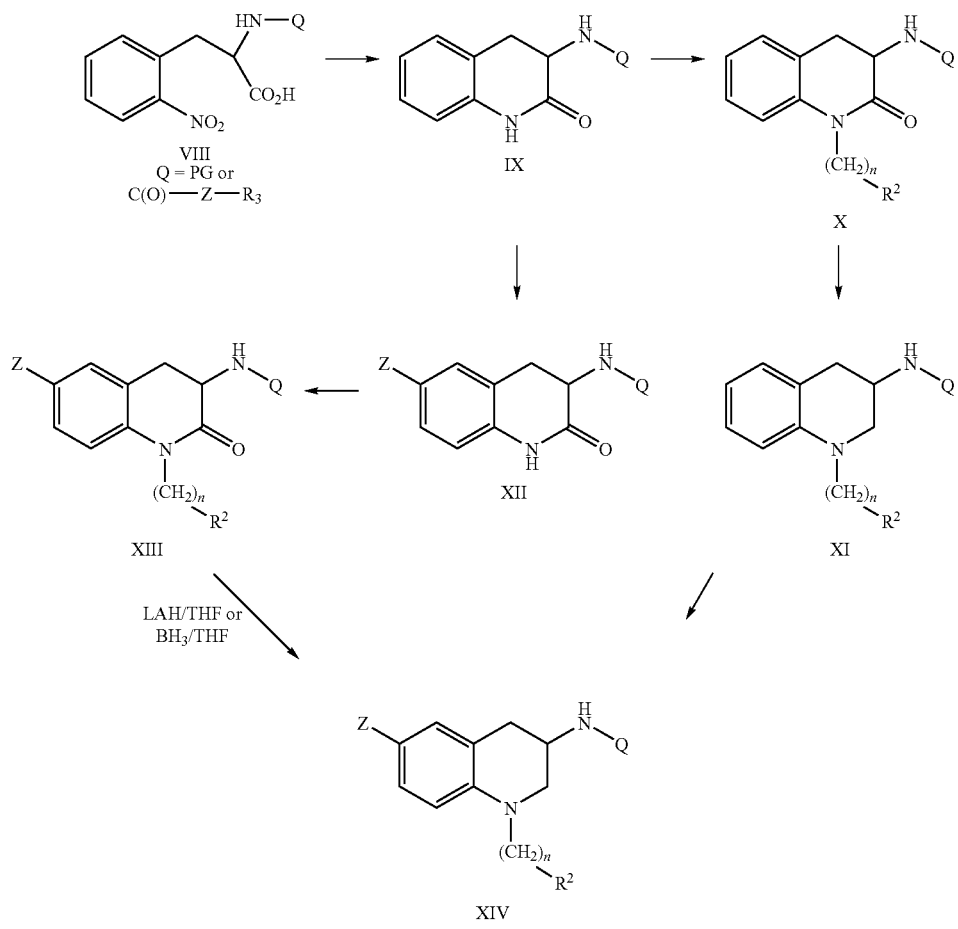

Scheme 3

Z = Br or Cl

As illustrated in Scheme 3, reduction of o-nitrophenylalanine derivative VIII via hydrogenation in the presence of a palladium catalyst in an alcoholic solvent, e.g., MeOH, affords lactam IX. Compound VIII in either a racemic or a homochiral form can be obtained commercially, or can be prepared by methods known in the literature, or can be readily prepared by one skilled in the art. Compounds of formula X can be prepared by reaction of IX with an alkylhalide in the presence of a base, e.g., cesium carbonate, or an arylhalide in the presence of a transition metal catalyst (e.g., palladium or copper). Compounds of formula M can be prepared by treating compound X with a reducing reagent (e.g., borane/THF complex or LAH/THF). Treatment of M with a bromination reagent (e.g., benzyltrimethylammonium tribromide) or a chlorination reagent (e.g., benzyltrimethylammonium dichloroiodate) in the presence of a base (e.g., calcium carbonate) provides compound XIV (Z=Br or Cl). Alternatively, treatment of intermediate IX with an appropriate bromination reagent or a chlorination reagent, such as the reagents mentioned above provides compound XII. Compounds of formula XIV can be prepared from XII following alkylation and reduction conditions analogous to those described for preparation of X and XI.

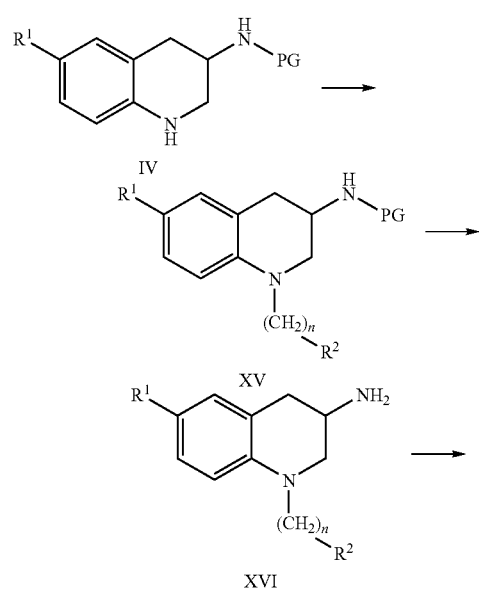

Scheme 4

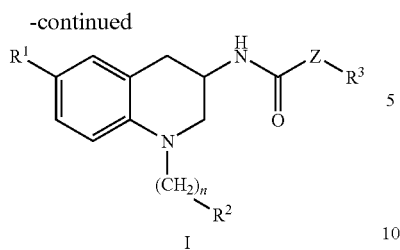

I

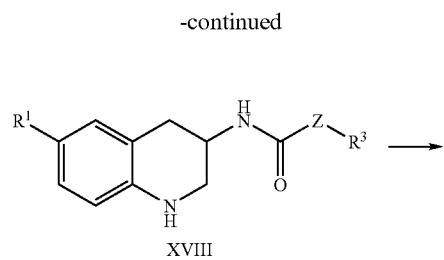

XVIII

As illustrated in Scheme 4, compounds of formula XV can be prepared by reductive amination of intermediate IV with an aldehyde in the presence of a reducing reagent (e.g., triethylsilane and trifluoroacetic acid, or sodium triacetoxyborohydride) or with an arylhalide in the presence of a transition metal catalyst (e.g., palladium or copper). Compounds of formula XVI can be prepared by removing the N-protection group (PG) under acidic (e.g., TFA for Boc-), basic (e.g., NaOH for amide), catalytic hydrogenation (for Cbz-) conditions. Compounds of formula I can be prepared by reacting amine XVI with an acylating reagent (e.g., acyl chloride, or a carboxylic acid for formation of amide), or a chloroformate (for formation of a carbamate), or an isocyanate (for formation of a urea).

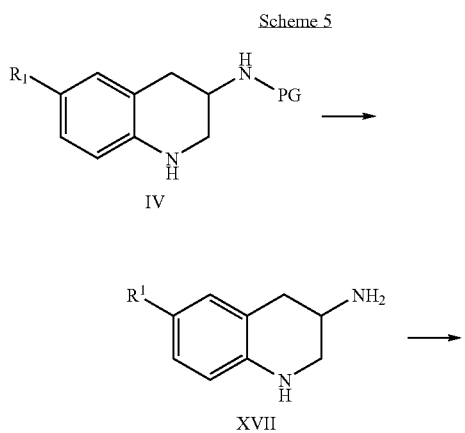

Alternatively, compounds of formula I can be prepared as shown in Scheme 5. Compounds of formula XVII can be prepared by removing the N-protection group (PG) in compound IV under acidic (e.g., TEA for Boc-), basic (e.g., NaOH for amide), catalytic hydrogenation (for Cbz-) conditions. Compounds of formula XVIII can be prepared by reacting amine XVII with an acylating reagent (e.g., acyl chloride, or a carboxylic acid for formation of amide), or a chloroformate (for formation of a carbamate), or an isocyanate (for formation of a urea). Compounds of formula I can be prepared by reductive amination of intermediate XVIII with an aldehyde in the presence of a reducing reagent (e.g., triethylsilane and trifluoroacetic acid, or sodium triacetoxyborohydride) or with an arylhalide in the presence of a transition metal catalyst (e.g., palladium or copper).

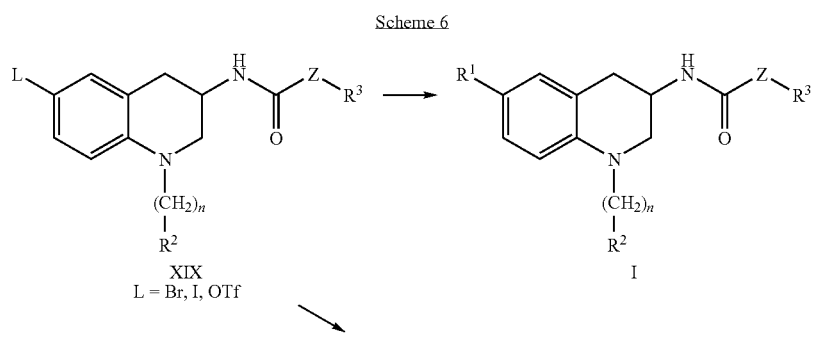

-continued

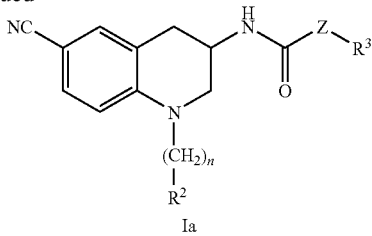

Ia

As illustrated in Scheme 6, compounds of formula I can be prepared via C—C bond formation by reacting intermediate XIX (where L is a leaving group, such as Br, I or sulfonate) with an activated $R^1$, such as an aryl or heteroaryl boronic acid, or an aryl or heteroaryl tin reagent in the presence of a palladium catalyst (e.g., $Pd(PPh_3)_4$). Compounds of formula I can also be prepared via C—N bond formation by treatment of intermediate XIX with a heterocyclic (e.g., a lactam, pyridone, imidazole or pyrazole) in the presence of a copper catalyst. Compounds of formula Ia can be prepared by treatment of intermediate XIX with zinc cyanide in the presence of a palladium catalyst, e.g., $Pd(Ph_3P)_4$.

EXAMPLES

The following examples serve to better illustrate, but not limit, some of the preferred embodiments of the invention.

Analytical HPLC and HPLC/MS Methods Employed in Characterization of Examples.

Analytical HPLC was performed on Shimadzu LC10AS liquid chromatographs.

Analytical HPLC/MS was performed on Shimadzu LC10AS liquid chromatographs and Waters ZMD Mass Spectrometers using the following methods:

Method A. Linear Gradient of 0 to 100% Solvent B Over 4 Min, with 1 Min Hold at 100% B
  UV visualization at 220 nm
  Column: Phenomenex Luna C1S 4.6×50 mm
  Flowrate: 4 ml/min Solvent A: 0.1% trifluoroacetic acid, 90% water, 10% methanol Solvent B: 0.1% trifluoroacetic acid, 90% methanol, 10% water Method B. Linear Gradient of 0 to 100% Solvent B Over 8 Min, with 3 Min Hold at 100% B
  UV visualization at 220 nm
  Column: Phenomenex Luna C18 4.6×75 mm or Zorbax SB C1S 4.6×75 mm
  Flow rate: 2.5 ml/min Solvent A: 0.2% phosphoric acid, 90% water, 10% methanol Solvent B: 0.2% phosphoric acid, 90% methanol, 10% water Method C. Linear Gradient of 10 to 100% Solvent B Over 2.50 Min, with 0.5 Min Hold at 100% B
  UV visualization at 220 nm
  Column: Xterra MS-C18, 2.1×50 mm
  Flow rate: 1.0 ml/min Solvent A: 0.1% trifluoroacetic acid, 100% water Solvent B: 0.1% trifluoroacetic acid, 100% acetonitrile NMR Employed in Characterization of Examples.

$^1H$ NMR spectra were obtained with Bruker or JOEL fourier transform spectrometers operating at the following frequencies: $^1H$ NMR: 400 MHz (Bruker), or 400 MHz (JOEL); $^{13}C$ NMR: 100 MHz (Bruker), or 100 MHz (JOEL). Spectra data are reported as Chemical shift (multiplicity, number of hydrogens, coupling constants in Hz) and are reported in ppm (δ units) relative to either an internal standard (tetramethylsilane=0 ppm) for $^1H$ NMR spectra, or are referenced to the residual solvent peak (2.49 ppm for $CD_2HSOCD_3$, 3.30 ppm for $CD_2HOD$, 7.24 ppm for $CHCl_3$, 39.7 ppm for $CD_3SOCD_3$, 49.0 ppm for $CD_3OD$, 77.0 ppm for $CDCl_3$). All $^{13}C$ NMR spectra were proton decoupled.

Example 1

(S)-3-Amino-1,2,3,4-tetrahydroquinoline-6-carbonitrile

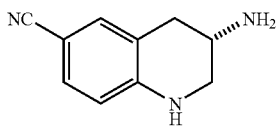

1A. tert-Butyl 1,2,3,4-tetrahydroquinolin-3-yl-carbamate

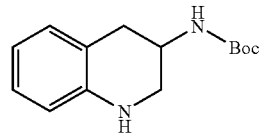

To a solution of 3-aminoquinoline (4.32 g, 30 mmol) in anhydrous THF (100 mL) under argon at RT was added dropwise sodium bis(trimethylsilyl)amide (1 M solution in THF, 63 mL, 63 mmol). The resulting dark brown mixture was treated with di-tert-butyl dicarbonate (7.2 g, 33 mmol). After stirring at RT for 2 h, the reaction was quenched with water (30 mL), and 1N aqueous HCl (45 mL). The aqueous layer was separated and extracted with EtOAc (2×70 mL). The combined organics were washed with saturated aqueous NaCl, dried $Na_2SO_4$) and concentrated. The residue was chromatographed (silica gel) eluting with EtOAc (0 to 50%) in hexanes to give 3-quinolinylcarbamic acid, 1,1-dimethylethyl ester (6.5 g, 89% yield) as an off-white solid.

To a solution of 3-quinolinylcarbamic acid, 1,1-dimethylethyl ester (6.0 g, 24.56 mmol) in MeOH (150 mL) was added acetic acid (18 mL). The mixture was bubbled with argon for 15 min, then palladium hydroxide (20 weight % palladium on carbon) (1.2 g) was added. The resulting suspension was subjected to hydrogenation under 45 psi of pressure for 16 h, then filtered. The filtrate was concentrated and the residue taken in CH$_2$Cl$_2$. The resulting CH$_2$Cl$_2$ solution was washed with saturated aqueous NaHCO$_3$, saturated aqueous NaCl, dried (Na$_2$SO$_4$) and concentrated. The residue was chromatographed (silica gel) eluting with EtOAc (0 to 50%) in hexanes to give 1A (4.6 g, 75% yield) as a white solid.

1B.
(6-Bromo-1,2,3,4-tetrahydroquinolin-3-yl)-carbamic acid tert-butyl ester

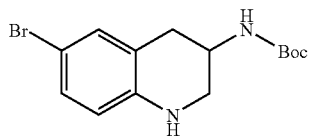

To a solution of tert-butyl 1,2,3,4-tetrahydroquinolin-3-yl-carbamate (2.7 g, 10.9 mmol), prepared as described in Example 1A, in THF (50 mL) at RT was added dropwise a solution of pyridinium tribromide (3.83 g, 0.41 mmol) in THF (50 mL). After addition, the reaction mixture was stirred for 15 min, then water (60 mL) and ether (60 mL) added. The aqueous layer was separated, and extracted with EtOAc (2×50 mL). The combined organics were washed with saturated aqueous NaCl, dried (Na$_2$SO$_4$) and concentrated. The residue was chromatographed (silica gel) eluting with EtOAc (0 to 50%) in hexanes to give the title compound (2.5 g, 70% yield) as a white solid.

1C.
(6-Cyano-1,2,3,4-tetrahydroquinolin-3-yl)-carbamic acid tert-butyl ester

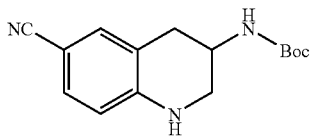

A solution of (6-bromo-1,2,3,4-tetrahydroquinolin-3-yl)-carbamic acid tert-butyl ester (250 mg, 0.76 mmol), prepared as described in Example 1B, and zinc cyanide (88 mg, 0.75 mmol) in DMF (2.5 mL) was bubbled with argon for 10 min, then tetrakis-(triphenylphosphine) palladium(0) (65 mg, 0.057 mmol) was added and the solution was deoxygenated. The reaction mixture was then heated at 90° C. for 4 h, cooled to RT, and partitioned between EtOAc and water. The aqueous layer was separated and extracted with EtOAc (2×20 mL). The combined EtOAc extracts were washed with saturated aqueous NaCl, dried Na$_2$SO$_4$) and concentrated. The residue was chromatographed (silica gel) eluting with EtOAc (0 to 60%) in hexanes to give the title compound (140 mg, 67% yield) as a white solid.

1D. 3-Amino-1,2,3,4-tetrahydroquinoline-6-carbonitrile, dihydrochloride

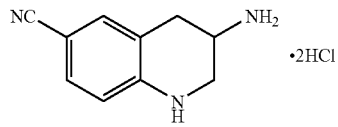

To a solution of (6-cyano-1,2,3,4-tetrahydroquinolin-3-yl)-carbamic acid tert-butyl ester (546 mg, 2 mmol), prepared as described in Example 1C, in CH$_2$Cl$_2$ (5 mL) at 0° C. was added 4 M HCl in dioxane (4 mL, 16 mmol). After addition, the reaction mixture was stirred at RT for 2 h, then concentrated. The residue was stripped with ether (3×), and the resulting off-white solid dried in vacuo to afford the title compound (490 mg, 100%).

1E. (S)-N-((S)-6-Cyano-1,2,3,4-tetrahydroquinolin-3-yl)-2-hydroxy-2-phenylacetamide

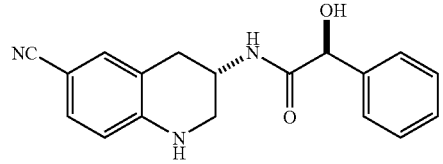

To a solution of 3-amino-1,2,3,4-tetrahydroquinoline-6-carbonitrile, dihydrochloride (10.03 g, 40.7 mmol), prepared as described in Example 1D, in DMF (100 mL) was added (S)-(+)-mandelic acid (7.45 g, 48.9 mmol), followed by EDAC (9.37 g, 48.9 mmol), HOBt (7.49 g, 48.9 mmol) and NMM (16.1 mL, 146.1 mmol). The reaction mixture was stirred at RT overnight, then diluted with EtOAc (200 mL), washed with water (50 mL×3), 1N aqueous HCl (50 mL), water (50 mL) and saturated aqueous NaCl, dried (Na$_2$SO$_4$) and concentrated. The residue was chromatographed (silica gel) eluting with EtOAc/hexanes (2:1 ratio), and the purified compound crystallized from acetone three times to give the title compound as the (S, S) diastereoisomer (2.54 g, 20% yield).

1F. (S)-3-Amino-1,2,3,4-tetrahydroquinoline-6-carbonitrile

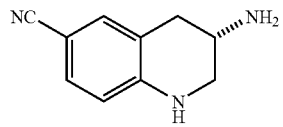

To a solution of (S)-N-((S)-6-cyano-1,2,3,4-tetrahydroquinolin-3-yl)-2-hydroxy-2-phenylacetamide (2.5 g, 8.14 mmol), prepared as described in Example 1E, in EtOH (25 mL) was added 15% aqueous sulfuric acid (25 mL). The resulting mixture was refluxed overnight, then cooled to RT. After removal of most of the EtOH, the mixture was diluted with water (200 mL), extracted with CH$_2$Cl$_2$ (3×50 mL). The aqueous layer was basified with 4N NaOH to pH=10, then extracted with CH₂Cl₂ (3×50 mL). The combined organics were washed with saturated aqueous NaCl dried (Na₂SO₄) and concentrated. The residue was crystallized from EtOAc/hexanes to afford the title compound (1.026 g, 73% yield). LC/MS (method A): retention time=0.95 min, (M+H)⁺=174.

Example 2

(R)-3-Amino-1,2,3,4-tetrahydroquinoline-6-carbonitrile

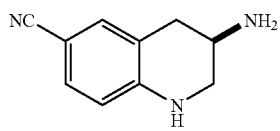

2A. (S)-N-((R)-6-Cyano-1,2,3,4-tetrahydroquinolin-3-yl)-2-hydroxy-2-phenylacetamide

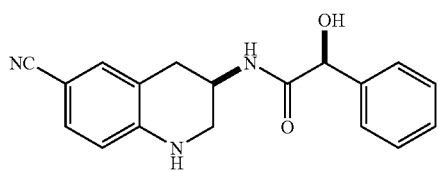

The title compound (S)-N-((R)-6-cyano-1,2,3,4-tetrahydroquinolin-3-yl)-2-hydroxy-2-phenylacetamide was isolated as the other (S, R) diastereomer as described in Example 1E.

2B. (R)-3-Amino-1,2,3,4-tetrahydroquinoline-6-carbonitrile

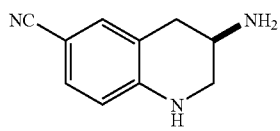

The title compound was prepared from the (S)-N-((R)-6-cyano-1,2,3,4-tetrahydroquinolin-3-yl)-2-hydroxy-2-phenylacetamide, prepared as described in Example 2A, by procedures analogous to those described in Example 1F. LC/MS (method A): retention time=0.95 min, (M+H)⁺=174.

Example 3

(S)-N-[1-(3-Chlorobenzyl)-6-cyano-1,2,3,4-tetrahydroquinolin-3-yl]-2-cyclohexylacetamide

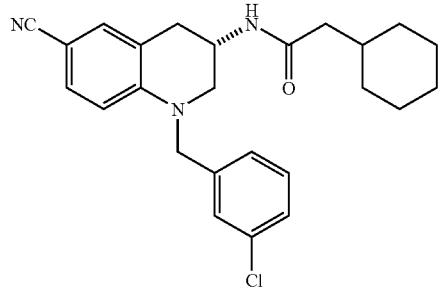

3A. N-[1-(3-Chlorobenzyl)-6-cyano-1,2,3,4-tetrahydroquinolin-3-yl]-carbamic acid tert-butyl ester

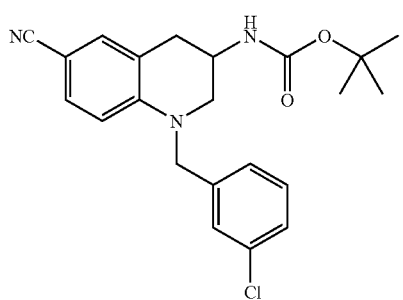

To a solution of (6-cyano-1,2,3,4-tetrahydroquinolin-3-yl)-carbamic acid tert-butyl ester (820 mg, 3 mmol), prepared as described in Example 1C, and 3-chloro benzaldehyde (0.34 mL, 3 mmol) in DCE (10 mL) was added NaBH(OAc)₃ (1.78 g, 8.4 mmol), followed by acetic acid (0-34 mL, 6 mmol). The reaction was stirred at RT for 16 h, then quenched with saturated aqueous NaHCO₃, extracted with CH₂Cl₂ (30 mL×3). The organic extracts were washed with water, saturated aqueous NaCl, dried (Na₂SO₄), and concentrated. The resulting residue was chromatographed (silica gel) eluting with EtOAc (10-50%) in hexanes to give the title compound (571 mg, 48%) as a foam.

3B. N-1-(3-Chlorobenzyl)-6-cyano-1,2,3,4-tetrahydroquinolin-3-yl)amine, trifluoroacetic acid salt

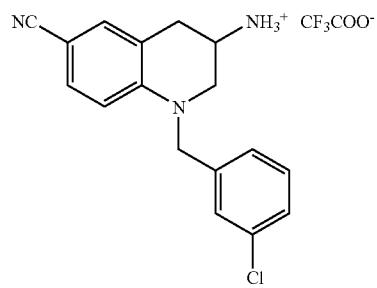

The solution of N-1-(3-chlorobenzyl)-6-cyano-1,2,3,4-tetrahydroquinolin 3-yl-carbamic acid tert-butyl ester (410 mg, 1.03 mmol), prepared as described in Example 3A, in CH₂Cl₂ (2 mL)-TFA (2 mL) was stirred at RT for 2 h, and then concentrated. The resulting residue was stripped with toluene (5 ml×2) and dried in vacuum to give the title compound (420 mg, 100%) as an oil.

3C. N-[1-(3-Chlorobenzyl)-6-cyano-1,2,3,4-tetrahydroquinolin-3-yl]-2-cyclohexyl-acetamide

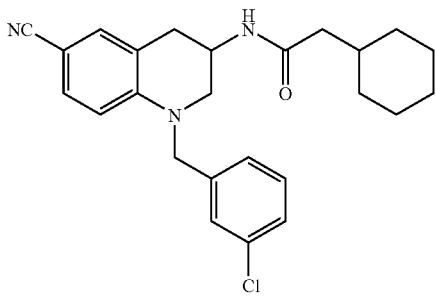

To a solution of N-1-(3-chlorobenzyl)-6-cyano-1,2,3,4-tetrahydroquinolin-3-yl)amine, trifluoroacetic acid salt (126 mg, 0.3 mmol), prepared as described in Example 3B, cyclohexyl acetic acid (51.2 mg, 0.36 mmol), EDAC (69 mg, 0.36 mmol) and HOBt (46 mg, 0.3 mmol) in DMF (2 mL) was added NMM (0.13 mL, 1.2 mmol). The reaction was stirred at RT for 16 h, then diluted with H₂O, extracted with EtOAc (20 mL×3). The organic extracts were washed with water, saturated aqueous NaCl, dried (Na₂SO₄), and concentrated. The resulting residue was chromatographed (silica gel) eluting with EtOAc (0-25%) in hexanes to give the title compound (70 mg, 55%) as a white solid. HPLC (method B): retention time=7.7 min, MS (ES): m/z 422 [M+H]⁺.

3D. (R)-N-[1-(3-Chlorobenzyl)-6-cyano-1,2,3,4-tetrahydroquinolin-3-yl]-2-cyclohexyl-acetamide

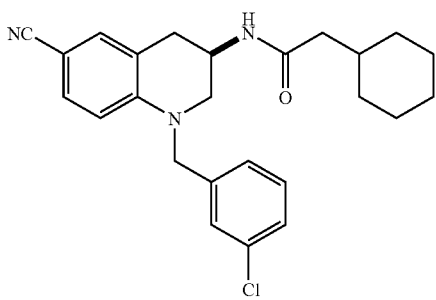

The title compound was separated from racemic N-[1-(3-chlorobenzyl)-6-cyano-1,2,3,4-tetrahydroquinolin-3-yl]-2-cyclohexylacetamide, prepared as described in Example 3C using chiral preparative HPLC (Conditions: Chiralpak AD, 5 cm×50 cm; eluted with 20% isopropanol in hexanes at 40 mL/min) as R-isomer. HPLC (method B): retention time=7.7 min, MS (ES): m/z 422 [M+H]⁺. Chiral HPLC: 100% e.e.; retention time=9.4 min; Conditions: AD (4.6×250 mm); Eluted with 20% isopropanol in hexanes for 30 min at 1 mL/min.

3E. (S)-N-[1-(3-Chlorobenzyl)-6-cyano-1,2,3,4-tetrahydroquinolin-3-yl]-2-cyclohexyl-acetamide

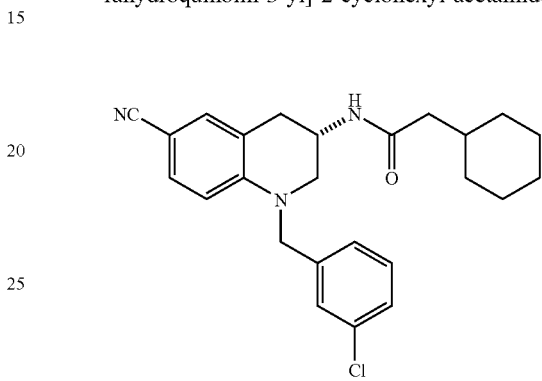

The title compound was separated from racemic N-[1-(3-chlorobenzyl)-6-cyano-1,2,3,4-tetrahydroquinolin-3-yl]-2-cyclohexylacetamide, prepared as described in Example 3C using chiral preparative HPLC (Conditions: Chiralpak AD, 5 cm×50 cm; eluted with 20% isopropanol in hexanes at 40 mL/min) as S-isomer. HPLC (method B): retention time 7.7 min, MS (ES): m/z 422 [M+H]⁺. Chiral HPLC 100% e.e.; retention time=13.4 min; Conditions: AD (4.6×250 mm); Eluted with 20% isopropanol in hexanes for 30 min at 1 mL/min.

Examples 4 to 18

Additional compounds were prepared by procedures analogous to those described in Example 3. The compounds of Examples 4 to 18 have the following structure,

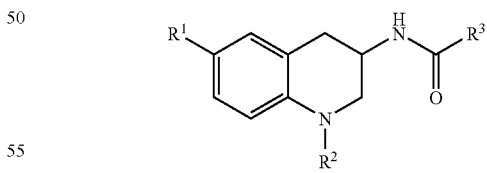

where the group R¹, R², R³, the stereochemistry, the compound name, retention time and molecular mass are set forth in Table 1. The chromatography techniques used to determine the compound retention times of Table 1 are as follows: HPLC (method B). LC-MS conditions (method A) (retention time reported using method A is specified with superscript a). The molecular mass of the compounds listed in Table 1, where provided, were determined by MS (ES) by the formula m/z.

TABLE 1

| Ex. No. | R¹ | R² | R³ | Compound Name | Retention Time (Min.)/Mass Specs [M + H]⁺ |
|---|---|---|---|---|---|
| 4 | CN | 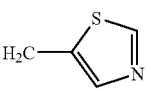 |  | (S)-N-(6-Cyano-1-thiazol-5-ylmethyl-1,2,3,4-tetrahydro-quinolin-3-yl) benzamide | 5.43/375 |
| 5 | CN | 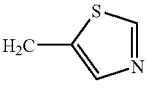 |  | (R)-N-(6-Cyano-1-thiazol-5-ylmethyl-1,2,3,4-tetrahydro-quinolin-3-yl) benzamide | 5.43/375 |
| 6 | CN | 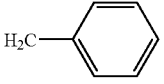 | 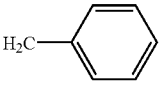 | (S)-N-(1-Benzyl-6-cyano-1,2,3,4-tetrahydroquinolin-3 yl)-2-phenylacetamide | 6.88/382 |
| 7 | CN | 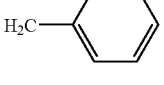 | 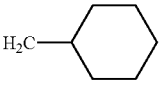 | (S)-N-(1-Benzyl-6-cyano-1,2,3,4-tetrahydroquinolin-3-yl)-2-cyclohexylacetamide | 7.52/388 |
| 8 | CN | 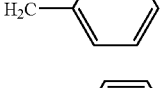 | 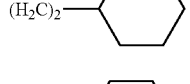 | (S)-N-(1-Benzyl-6-cyano-1,2,3,4-tetrahydroquinolin-3-yl)-3-cyclohexyl-propionamide | 4.75$^a$/405 |
| 9 | CN | 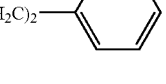 | 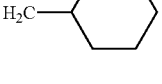 | N-(6-Cyano-1-phenethyl-1,2,3,4-tetrahydroquinolin-3-yl)-2-cyclohexylacetamide | 7.84/402 |
| 10 | CN | 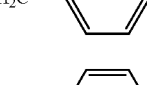 | 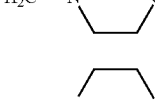 | (S)-N-(1-Benzyl-6-cyano-1,2,3,4-tetrahydroquinolin-3-yl)-2-morpholin-4-yl-acetamide | 5.05/391 |
| 11 | CN | 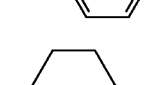 | 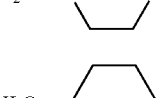 | (R)-N-(1-Benzyl-6-cyano-1,2,3,4-tetrahydroqninolin-3-yl)-2-morpholin-4-yl-acetamide | 5.04/391 |
| 12 | CN |  | 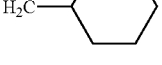 | N-(6-Cyano-1-cyclohexyl-1,2,3,4-tetrahydroquinolin-3-yl)-2-cyclohexylacetamid | 6.94/380 |
| 13 | Ph | 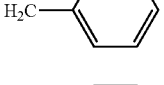 | 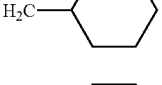 | N-(1-Benzyl-6-phenyl-1,2,3,4-tetrahydroquinolin-3-yl)-2-cyclohexylacetamide | 8.80/439 |
| 14 | Br | 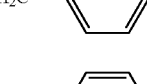 | 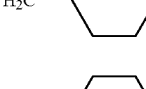 | (S)-N-(1-Benzyl-6-bromo-1,2,3,4-tetrahydroquinolin-3-yl)-2-cyclohexylacetamide | 8.40/442 |
| 15 | Br | 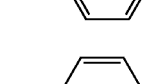 | 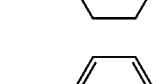 | (R)-N-(1-Benzyl-6-bromo-1,2,3,4-tetrahydroquinolin-3-yl)-2-cyclohexylacetamide | 8.39/442 |
| 16 | CN | 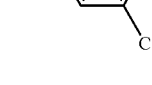 |  | (S)-N-[1-(3-Chloro-benzyl)-6-cyano-1,2,3,4-tetrahydroquinolin-3-yl]-2-phenylacetamide | 7.16/416 |
| 17 | CN | 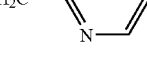 | 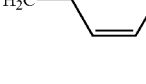 | (S)-N-(6-Cyano-1-pyridin-2-ylmethyl-1,2,3,4-tetrahydro-quinolin-3-yl)-2-phenyl acetamide | 4.67/383 |

TABLE 1-continued

| Ex. No. | R¹ | R² | R³ | Compound Name | Retention Time (Min.)/Mass Specs [M + H]⁺ |
|---|---|---|---|---|---|
| 18 | CN | H₂C–(phenyl)–⸜ | ⸜–C(CH₃)₂–O–(pyridin-2-yl with 5-CF₃) | N-(1-benzyl-6-cyano-1,2,3,4-tetrahydroquinolin-3-yl)-2-methyl-2-(5-(trifluoromethyl)pyridin-2-yloxy)propanamide | 3.80ᵃ/495 |

Example 19

1-Benzyl-6-chloro-1,2,3,4-tetrahydroquinolin-3-amine, dihydrochloride

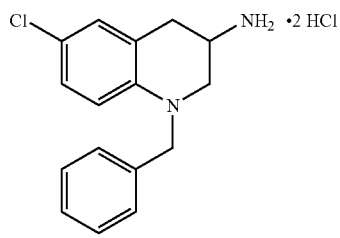

19A. tert-Butyl 6-chloro-1,2,3,4-tetrahydroquinolin-3-ylcarbamate

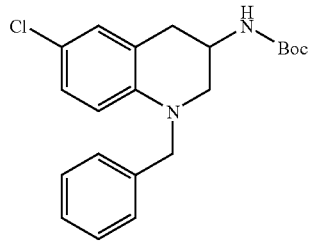

To a solution of tert-butyl 1,2,3,4-tetrahydroquinolin-3-ylcarbamate (28.3 g, 114 mmol), prepared as described in Example 1A, in acetonitrile (240 mL) at RT was added dropwise a solution of N-chlorosuccinimide (15.22 g, 114 mmol) in acetonitrile (240 mL). After addition, the reaction mixture was stirred for 6 h, then water (500 mL) added. The mixture was extracted with EtOAc (2×500 mL). The combined organics were washed with saturated aqueous NaCl, dried Na₂SO₄) and concentrated. The residue was chromatographed (silica gel) eluting with EtOAc/hexanes (1:5 ratio) to give the title compound (10.6 g, 58% yield) as a white solid.

19B. tert-Butyl 1-benzyl-6-chloro-1,2,3,4-tetrahydroquinolin-3-ylcarbamate

To a solution of tert-butyl 6-chloro-1,2,3,4-tetrahydroquinolin-3-ylcarbamate (310 mg, 1.096 mmol), prepared as described in Example 19A, in 1,2-dichloroethane (7 mL) was added benzaldehyde (235 mg, 2.193 mmol), followed by sodium triacetoxyborohydride (650 mg, 3.069 mmol) and AcOH (200 mg, 3.29 mmol). The reaction mixture was stirred at RT for 4 h, then diluted with EtOAc, washed with saturated aqueous NaHCO₃, water, saturated aqueous NaCl, dried Na₂SO₄) and concentrated. The resulting residue was chromatographed (silica gel) eluting with EtOAc/hexanes (1:5 ratio) to give the title compound as light yellow foam (325 mg, 80%).

19C. 1-Benzyl-6-chloro-1,2,3,4-tetrahydroquinolin-3-amine, dihydrochloride

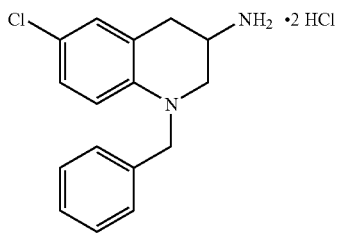

The title compound was prepared from tert-butyl 1-benzyl-6-chloro-1,2,3,4-tetrahydroquinolin-3-ylcarbamate, prepared as described in Example 19B, by procedures analogous to those described in Example 1D.

Example 20

3-(Benzo[d][1,3]dioxol-5-yl)-N-(1-benzyl-6-chloro-1,2,3,4-tetrahydroquinolin-3-yl)propanamide

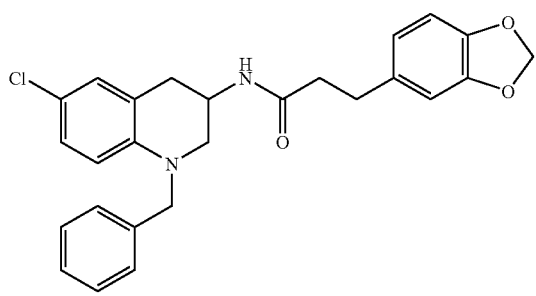

The title compound was synthesized as part of library using the following procedure in a parallel synthesis fashion using 48 well red and blue minireactors.

Typical procedure: To a suspension of PS-DIC 110 mg/well (Argonaut, 1.38 mmol/g loading) in DCE (0.5 mL) at room temperature was added HOBt (5 mg in 100 μL DMF), followed by 3-(benzo[d][1,3]dioxol-5-yl)propanoic acid (75 μmol). To this was added 1-benzyl-6-chloro-1,2,3,4-tetrahydroquinolin-3-amine, dihydrochloride (14 mg, 50 μmol), prepared as described in Example 19C, in 1,2-dichloroethane (0.5 mL). The reaction mixture was shaken at RT for 24 h, contents were filtered into a synthesis tube rack (STR) and the solvent was dried in a speed vac. The resulting residue was chromatographed using preparative HPLC (conditions: Xterra MS-C18 (30×50 mm); eluted with 10% to 100% B, 6 min gradient. (A=100% water with 0.1% TFA and B=acetonitrile with 0.1% TFA); flow rate at 30 mL/min; UV detection at 220 nm) to give the title compound, 3-(benzo[d][1,3]dioxol-5-yl)-N-(1-benzyl-6-chloro-1,2,3,4-tetrahydroquinolin-3-yl)propanamide, (2.2 mg, 8%). HPLC (method C): retention time=1.6 min, MS (ES): m/z 449 [M+H]$^+$.

Examples 21 to 28

Additional compounds were prepared by procedures analogous to those described in Example 20. The compounds of Examples 21 to 28 have the following structure,

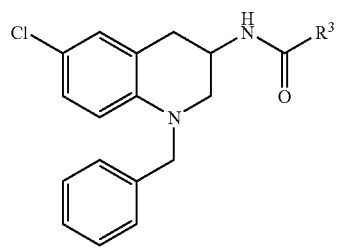

where the group R$^3$, the compound name, retention time and molecular mass are set forth in Table 2. The chromatography techniques used to determine the compound retention times of Table 2 are as follows. LC-MS conditions (method C). The molecular mass of the compounds listed in Table 2, where provided, were determined by MS (ES) by the formula m/z.

TABLE 2

| Example Number | R$^3$ | Compound Name | Retention Time (Min.)/ Mass Specs [M + H]$^+$ |
|---|---|---|---|
| 21 | | N-(1-benzyl-6-chloro-1,2,3,4-tetrahydroquinolin-3-yl)-2-(benzyloxy)propanamide | 1.74/435 |
| 22 | | N-(1-benzyl-6-chloro-1,2,3,4-tetrahydroquinolin-3-yl)-2-(2-methoxyphenyl)acetamide | 1.67/421 |
| 23 | | N-(1-benzyl-6-chloro-1,2,3,4-tetrahydroquinolin-3-yl)-3-(3-methoxyphenyl)propanamide | 1.75/435 |

TABLE 2-continued

| Example Number | R³ | Compound Name | Retention Time (Min.)/ Mass Specs [M + H]⁺ |
|---|---|---|---|
| 24 | | N-(1-benzyl-6-chloro-1,2,3,4-tetrahydroquinolin-3-yl)-2-(3,5-dimethoxyphenyl)acetamide | 1.60/451 |
| 25 | | 3-(benzo[d][1,3]dioxol-5-yl)-N-(1-benzyl-6-chloro-1,2,3,4-tetrahydroquinolin-3-yl)propanamide | 1.60/449 |
| 26 | | N-(1-benzyl-6-chloro-1,2,3,4-tetrahydroquinolin-3-yl)-2-(1,3-dioxoisoindolin-2-yl)propanamide | 1.71/474 |
| 27 | | tert-butyl 2-((1-benzyl-6-chloro-1,2,3,4-tetrahydroquinolin-3-yl)carbamoyl)benzoate | 1.84/477 |
| 28 | | N-(1-benzyl-6-chloro-1,2,3,4-tetrahydroquinolin-3-yl)-2-(1H-pyrrol-1-yl)benzamide | 1.76/442 |

Example 29

(2R)-N-(1-Benzyl-6-(4-fluorophenyl)-1,2,3,4-tetrahydroquinolin-3-yl)-2-hydroxy-3-phenylpropanamide

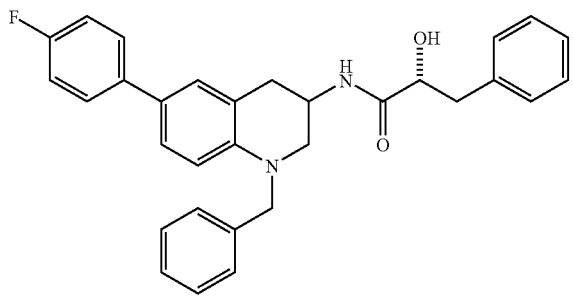

29A. (1-Benzyl-6-bromo-1,2,3,4-tetrahydroquinolin-3-yl)-carbamic acid tert-butyl ester

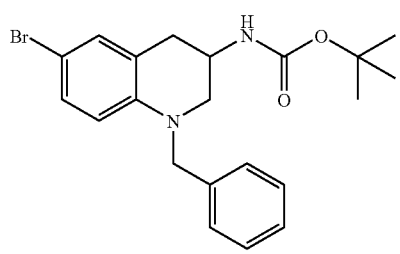

To a solution of (6-bromo-1,2,3,4-tetrahydroquinolin-3-yl)-carbamic acid tert-butyl ester (1.636 g, 5 mmol), prepared as described in Example 1B, in DCE (16 mL) at RT was added benzaldehyde (1 mL, 10 mmol), followed by NaBH(OAc)$_3$ (2.97 g, 14 mmol) and AcOH (0.6 mL, 10 mmol). The reaction mixture was stirred at RT for 16 h, then quenched with aqueous NaHCO$_3$ (40 mL) and extracted with CH$_2$Cl$_2$ (50 mL×3). The combined extracts were washed with saturated aqueous NaCl, dried (Na$_2$SO$_4$), and concentrated. The resulting residue was chromatographed (silica gel) eluting with 0-20% of EtOAc in hexanes to give the title compound (1.70 g, 81%) as a white foam.

29B. (tert-Butyl 1-benzyl-6-(4-fluorophenyl)-1,2,3,4-tetrahydroquinolin-3-ylcarbamate

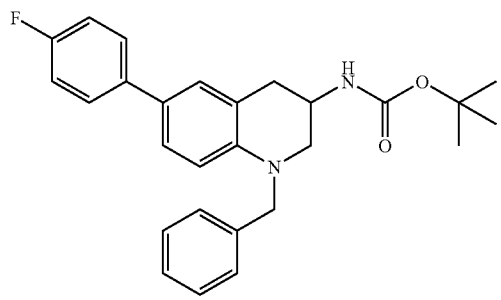

(1-Benzyl-6-bromo-1,2,3,4-tetrahydroquinolin-3-yl)-carbamic acid tert-butyl ester (2.00 g, 4.79 mmol), prepared as described in Example 29A, 4-fluorophenyl-boronic acid (2.01 g, 14.37 mmol) and K$_2$CO$_3$ (2.65 g, 19.16 mmol) in a mixed solvent of THF (50 mL) and MeOH (25 mL) were stirred at RT for 30 min while N$_2$ was allowed to bubble through the mixture, and then PXPd (258 mg, 0.48 mmol) was added. The reaction mixture was heated at 60° C. under N$_2$ for 3 h. After cooling to RT, the solvent was stripped and the residue was diluted with H$_2$O (60 mL) and CH$_2$Cl$_2$ (100 mL). The aqueous layer was extracted with CH$_2$Cl$_2$ (100 mL×3), and the combined organic extracts were washed with saturated aqueous NaCl (50 mL), dried (Na$_2$SO$_4$), filtered and concentrated. The resulting residue was chromatographed (silica gel) eluting with EtOAc (0-20%) in hexanes to give the title compound (1.11 g, 54%) as a white foam.

29C. 1-Benzyl-6-phenyl-1,2,3,4-tetrahydroquinolin-3-ylamine, trifluoroacetic acid salt

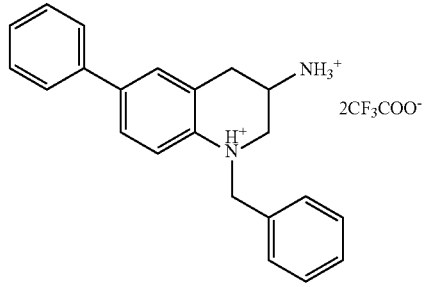

To a solution of (tert-butyl 1-benzyl-6-(4-fluorophenyl)-1,2,3,4-tetrahydroquinolin-3-ylcarbamate (1.11 g, 2.57 mmol), prepared as described in Example 29B, in CH$_2$Cl$_2$ (13 mL) at RT was added trifluoroacetic acid (13 mL). After stirring at RT for 2 h, the reaction mixture was concentrated, and the resulting residue stripped with toluene, dried in vacuo to give the title compound as a brown solid (1.44 g, 100%).

29D. (2R)-N-(1-Benzyl-6-(4-fluorophenyl)-1,2,3,4-tetrahydroquinolin-3-yl)-2-hydroxy-3-phenylpropanamide

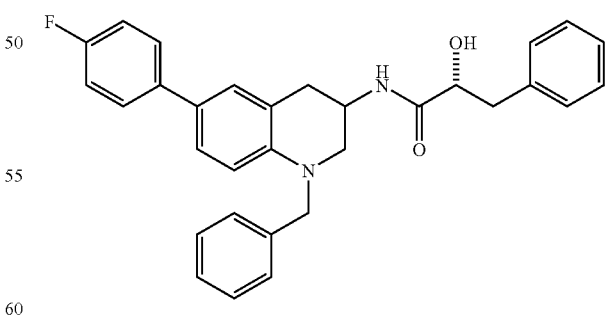

To a solution of D-(+)-3-phenyllactic acid (12 mg, 0.07 mmol), EDAC (13 mg, 0.07 mmol), HOBt (11 mg, 0.07 mmol) and DIPEA (31 µL, 0.18 mmol) in CH$_2$Cl$_2$ (0.6 mL) was added 1-benzyl-6-phenyl-1,2,3,4-tetrahydroquinolin-3-ylamine, trifluoroacetic acid salt (35 mg, 0.06 mmol), prepared as described in Example 29C. The resulting mixture was stirred at RT for overnight. The solvent was evaporated and the residue purified by Prep. HPLC to give the title compound (7.1 mg, 24%) as a beige solid. HPLC (method A): retention time=4.20 min, MS (ES): [M+1]+=481.

Example 30

(2S)—N-(1-Benzyl-6-(4-fluorophenyl)-1,2,3,4-tetrahydroquinolin-3-yl)-2-hydroxy-3-phenylpropanamide

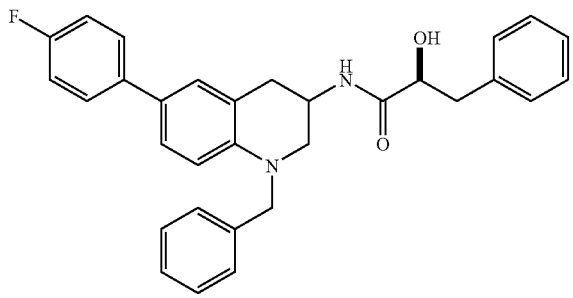

To a solution of L-(−)-3-phenyllacetic acid (13 mg, 0.08 mmol), EDAC (15 mg, 0.08 mmol), HOBt (12 mg, 0.08 mmol) and DIPEA (36 µL, 0.21 mmol) in CH$_2$Cl$_2$ (0.7 mL) was added 1-benzyl-6-phenyl-1,2,3,4-tetrahydroquinolin-3-ylamine, trifluoroacetic acid salt (40 mg, 0.07 mmol), prepared as described in Example 29C. The resulting mixture was stirred at RT for overnight. The solvent was evaporated and the residue purified by Prep. HPLC to give the title compound (22 mg, 64%) as a white solid. HPLC (Method A): retention time=4.19 min, MS (ES): [M+1]+=481.

Examples 31 to 40

Additional compounds were prepared by procedures analogous to those described in Example 29. The compounds of Examples 31 to 40 have the following structure,

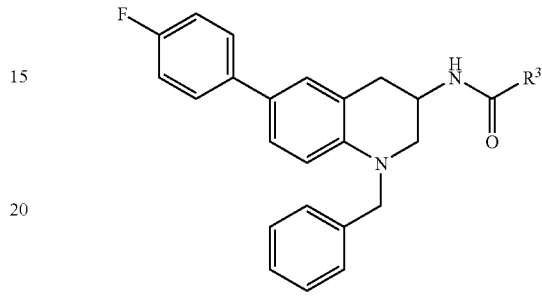

where the group R$^3$, the stereochemistry, the compound name, retention time and molecular mass are set forth in Table 3. The chromatography techniques used to determine the compound retention times of Table 3 are as follows: LC-MS conditions (method A). The molecular mass of the compounds listed in Table 3, where provided, were determined by MS (ES) by the formula m/z.

TABLE 3

| Example Number | R$^3$ | Compound Name | Retention Time (Min.)/ Mass Specs [M + H]+ |
|---|---|---|---|
| 31 | | (2S)-N-(1-benzyl-6-(4-fluorophenyl)-1,2,3,4-tetrahydroquinolin-3-yl)-2-hydroxy-4-phenylbutanamide | 3.49/495 |
| 32 | | N-(1-benzyl-6-(4-fluorophenyl)-1,2,3,4-tetrahydroquinolin-3-yl)-2-hydroxy-3-(1H-indol-2-yl)propanamide | 4.09/520 |
| 33 | | N-(1-benzyl-6-(4-fluorophenyl)-1,2,3,4-tetrahydroquinolin-3-yl)-3-(2-methoxyphenyl)propanamide | 4.28/495 |
| 34 | | N-(1-benzyl-6-(4-fluorophenyl)-1,2,3,4-tetrahydroquinolin-3-yl)-3-(3-methoxyphenyl)propanamide | 4.28/495 |

TABLE 3-continued

| Example Number | R³ | Compound Name | Retention Time (Min.)/ Mass Specs [M + H]⁺ |
|---|---|---|---|
| 35 | (4-methoxyphenyl)ethyl group | N-(1-benzyl-6-(4-fluorophenyl)-1,2,3,4-tetrahydroquinolin-3-yl)-3-(4-methoxyphenyl)propanamide | 4.24/495 |
| 36 | (2-hydroxyphenyl)ethyl group | N-(1-benzyl-6-(4-fluorophenyl)-1,2,3,4-tetrahydroquinolin-3-yl)-3-(2-hydroxyphenyl)propanamide | 4.13/481 |
| 37 | (3-hydroxyphenyl)ethyl group | N-(1-benzyl-6-(4-fluorophenyl)-1,2,3,4-tetrahydroquinolin-3-yl)-3-(3-hydroxyphenyl)propanamide | 4.06/481 |
| 38 | (4-hydroxyphenyl)ethyl group | N-(1-benzyl-6-(4-fluorophenyl)-1,2,3,4-tetrahydroquinolin-3-yl)-3-(4-hydroxyphenyl)propanamide | 4.01/481 |
| 39 | phenylethyl group | N-(1-benzyl-6-(4-fluorophenyl)-1,2,3,4-tetrahydroquinolin-3-yl)-3-phenylpropanamide | 4.26/465 |
| 40 | 2-methyl-2-(5-(trifluoromethyl)pyridin-2-yloxy)propyl group | N-(1-benzyl-6-(4-fluorophenyl)-1,2,3,4-tetrahydroquinolin-3-yl)-2-methyl-2-(5-(trifluoromethyl)pyridin-2-yloxy)propanamide | 4.39/564 |

Example 41

(S)-1-[1-(3-Chlorobenzyl)-6-cyano-1,2,3,4-tetrahydroquinolin-3-yl]-3-phenylurea

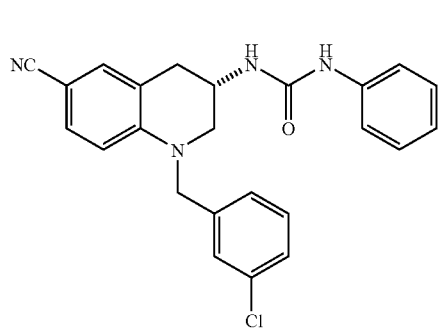

41A. (S)-(6-Cyano-1,2,3,4-tetrahydroquinolin-3-yl)-3-phenylurea

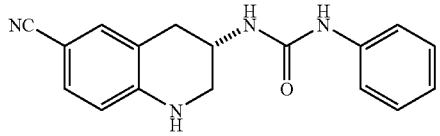

To a solution of (S)-3-amino-1,2,3,4-tetrahydroquinoline-6-carbonitrile (52 mg, 0.3 mmol), prepared as described in Example 1F, in CH$_2$Cl$_2$ (2 mL) at RT was added phenyl isocyanate (33 μl, 0.3 mmol) dropwise. After addition, the reaction was stirred at RT for 1 h. The product was collected by filtration and washed with CH$_2$Cl$_2$-hexanes (1:1) to give the title compound (85 mg, 97%) as a white solid.

41B. (S)-1-[1-(3-Chlorobenzyl)-6-cyano-1,2,3,4-tetrahydroquinolin-3-yl]-3-phenylurea

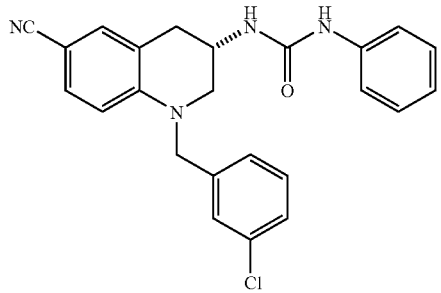

The title compound was prepared from (S)-(6-cyano-1,2,3,4-tetrahydroquinolin-3-yl)-3-phenylurea, prepared as described in Example 41A, and 3-chlorobenzaldehyde by procedures analogous to those described in Example 3A. HPLC (method B): retention time 7.2 min. MS (ES): m/z 417 [M+H]$^+$. Chiral HPLC 100% e.e.; retention time=27.3 min; Conditions: AD (4.6×250 mm); Eluted with 20% isopropanol in hexanes for 60 min at 1 mL/min.

Example 42

(S)-1-[1-(3-Chloro-benzyl)-6-cyano-1,2,3,4-tetrahydroquinolin-3-yl]-3-cyclohexylurea

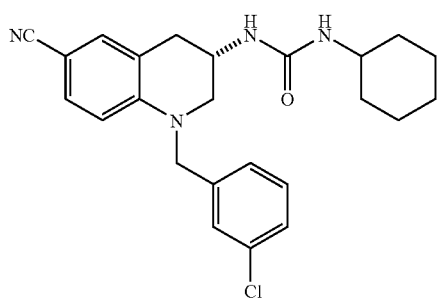

42A. (S)-1-[6-Cyano-1,2,3,4-tetrahydroquinolin-3-yl]-3-cyclohexyl-urea

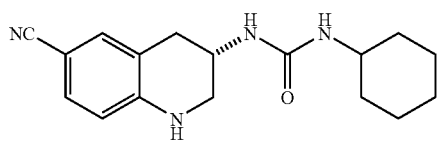

The title compound was prepared from (S)-3-amino-1,2,3,4-tetrahydroquinoline-6-carbonitrile (52 mg, 0.3 mmol), prepared as described in Example 1F, and cyclohexyl isocyanate by procedures analogous to those described in Example 41A.

42B. (S)-1-[1-(3-Chlorobenzyl)-6-cyano-1,2,3,4-tetrahydroquinolin-3-yl]-3-cyclohexylurea

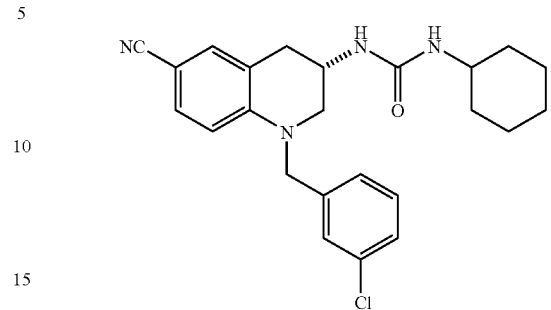

The title compound was prepared from (S)-1-[6-cyano-1,2,3,4-tetrahydroquinolin-3-yl]-3-cyclohexyl-urea, prepared as described in Example 42A, and 3-chlorobenzaldehyde by procedures analogous to those described in Example 3A. HPLC (method B): retention time=7.50 min. MS (ES): m/z 423 [M+H]$^+$. Chiral HPLC 100% e.e.; retention time=12.2 min; Conditions: AD (4.6×250 mm); Eluted with 20% isopropanol in hexanes for 30 min at 1 mL/min.

Example 43

(S)-[1-(3-Chlorobenzyl)-6-cyano-1,2,3,4-tetrahydroquinolin-3-yl]-carbamic acid cyclohexyl ester

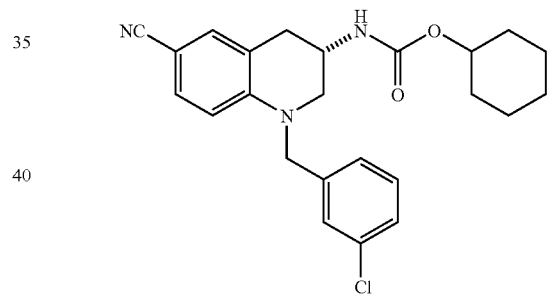

43A. Cyclohexyl 4-nitrophenyl carbonate

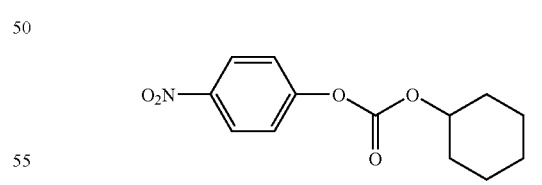

To a solution of cyclohexanol (1.0 g, 10 mmol) in THF (20 mL) at 0° C. was added pyridine (0.97 mL, 12 mmol). After 5 min stirring under N$_2$, a solution of 4-nitrophenyl chloroformate (2.2 g, 11 mmol) in THF (15 mL) was added slowly. After addition, the reaction mixture was stirred at 0° C. for 30 min, and then at RT for 3 h. The precipitate was filtered, the filtrate was concentrated. The resulting residue was chromatographed (40 g silica gel) eluting with EtOAc (0-20%) in hexanes to give the title compound (2.4 g, 91%) as a white solid.

43B. [1-(3-Chlorobenzyl)-6-cyano-1,2,3,4-tetrahydroquinolin-3-yl]-carbamic acid cyclohexyl ester

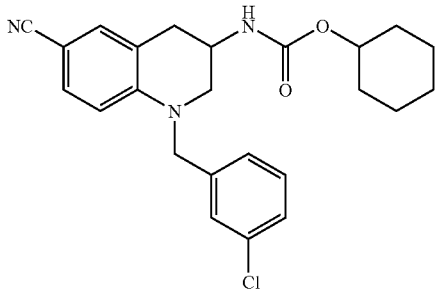

To a solution of N-1-(3-chlorobenzyl)-6-cyano-1,2,3,4-tetrahydroquinolin-3-yl)amine, trifluoroacetic acid salt (412 mg, 1.0 mmol), prepared as described in Example 3B, in THF (4 mL) at RT was added Et₃N (0.28 mL, 2.0 mmol), followed by cyclohexyl 4-nitrophenyl carbonate (292 mg, 1.1 mmol), prepared as described in Example 43A. After addition, the mixture was stirred at RT for 16 h, and then diluted with EtOAc (30 mL), washed with water, 1N aqueous NaOH, saturated aqueous NaCl, dried Na₂SO₄), and concentrated. The resulting residue was chromatographed (40 g silica gel) eluting with EtOAc (0-25%) in hexanes to give the title compound (280 mg, 66%) as a white solid. HPLC (method B): retention time=8.00 min. MS (ES): m/z 424 [M+H]⁺.

43C. (S)-[1-(3-Chlorobenzyl)-6-cyano-1,2,3,4-tetrahydroquinolin-3-yl]-carbamic acid cyclohexyl ester

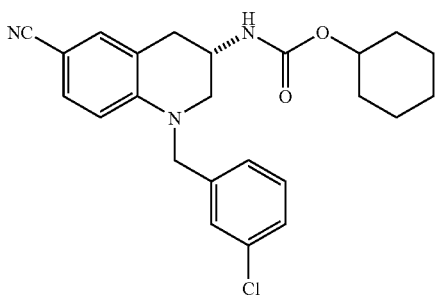

The title compound was separated from racemic [1-(3-chlorobenzyl)-6-cyano-1,2,3,4-tetrahydroquinolin-3-yl]-carbamic acid cyclohexyl ester, prepared as described in Example 43B, using chiral preparative HPLC (conditions: Chiralpak AD, 5×50 cm; eluted with 20% isopropanol in hexanes at 40 mL/min). HPLC (method B): retention time 8.15 min. MS (ES): m/z 424 [M+H]⁺. Chiral HPLC 100% e.e.; retention time=6.16 min; Conditions: OD (4.6×250 mm); Eluted with 40% isopropanol in hexanes for 30 min at 1 mL/min.

Example 44

(R)-[1-(3-Chlorobenzyl)-6-cyano-1,2,3,4-tetrahydroquinolin-3-yl]-carbamic acid cyclohexyl ester

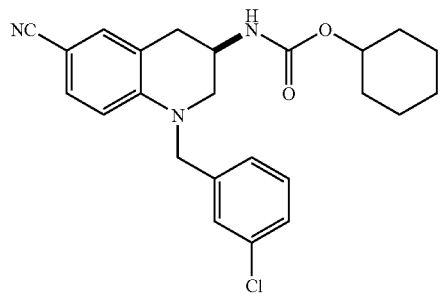

The title compound was separated from racemic [1-(3-chlorobenzyl)-6-cyano-1,2,3,4-tetrahydroquinolin-3-yl]-carbamic acid cyclohexyl ester, prepared as described in Example 43B, using chiral preparative HPLC (conditions: Chiralpak AD, 5×50 cm; eluted with 20% isopropanol in hexanes at 40 mL/min). HPLC (method B): retention time 8.15 min. MS (ES): m/z 424 [M+H]⁺. Chiral HPLC 100% e.e.; retention time=4.87 min; Conditions: OD (4.6×250 mm); Eluted with 40% isopropanol in hexanes for 30 min at 1 mL/min.

Examples 44 to 51

Additional compounds were prepared by procedures analogous to those described in Example 43. The compounds of Examples 44 to 51 have the following structure,

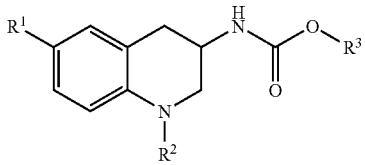

where the group $R^1$, $R^2$, $R^3$, the stereochemistry, the compound name, retention time and molecular mass are set forth in Table 4. The chromatography techniques used to determine the compound retention times of Table 4 are as follows: HPLC conditions: (method B) and LC-MS conditions: (method A). The molecular mass of the compounds listed in Table 4, where provided, were determined by MS (ES) by the formula m/z.

TABLE 4

| Ex. No. | R¹ | R² | R³ | Compound Name | Retention Time (Min.)/Mass Specs [M + H]⁺ |
|---|---|---|---|---|---|
| 44 | CN | H₂C–Ph | cyclohexyl | (1-Benzyl-6-cyano-1,2,3,4-tetrahydroquinolin-3-yl)-carbamic acid cyclohexyl ester | 8.05/390 |
| 45 | CN | H₂C–Ph | cyclohexyl | (S)-(1-Benzyl-6-cyano-1,2,3,4-tetrahydroquinolin-3-yl)-carbamic acid cyclohexyl ester | 8.05/390 |
| 46 | CN | H₂C–Ph | cyclohexyl | (R)-(1-Benzyl-6-cyano-1,2,3,4-tetrahydroquinolin-3-yl)-carbamic acid cyclohexyl ester | 8.04/390 |
| 47 | CN | H₂C–Ph | H₂C–Ph | (S)-(1-Benzyl-6-cyano-1,2,3,4-tetrahydroquinolin-3-yl)-carbamic acid benzyl ester | 7.51/398 |
| 48 | CN | H₂C–Ph | H₂C–Ph | (R)-(1-Benzyl-6-cyano-1,2,3,4-tetrahydroquinolin-3-yl)-carbamic acid benzyl ester | 7.52/398 |
| 49 | CN | H₂C–Ph | tetrahydropyran-4-yl | (S)-(1-Benzyl-6-cyano-1,2,3,4-tetrahydroquinolin-3-yl)-carbamic acid tetrahydro-pyran-4-yl ester | 7.22/392 |
| 50 | CN | (H₂C)₂–Ph | cyclohexyl | (6-Cyano-1-phenethyl-1,2,3,4-tetrahydroquinolin-3-yl)-carbamic acid cyclohexyl ester | 7.24/404 |
| 51 | Br | H₂C–Ph | cyclohexyl | (1-Benzyl-6-bromo-1,2,3,4-tetrahydroquinolin-3-yl)-carbamic acid cyclohexyl ester | 8.83/444 |

Example 52

(1-Benzyl-6-cyano-1,2,3,4-tetrahydroquinolin-3-yl)-carbamic acid 4-hydroxycyclohexyl ester

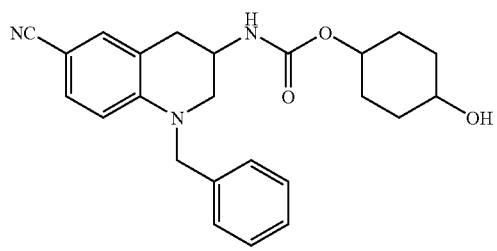

52A. N-1-Benzyl-6-cyano-1,2,3,4-tetrahydroquinolin-3-yl)-amine, hydrochloride salt

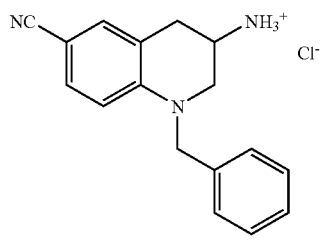

The title compound was prepared from (6-cyano-1,2,3,4-tetrahydroquinolin-3-yl)-carbamic acid tert-butyl ester, prepared as described in Example 1C, and benzaldehyde by procedures analogous to those described in Example 3A and 31.

52A. (1-Benzyl-6-cyano-1,2,3,4-tetrahydroquinolin-3-yl)-carbamic acid 4-hydroxy-cyclohexyl ester

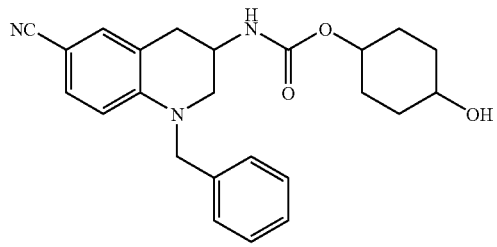

To a stirring suspension of N-1-benzyl-6-cyano-1,2,3,4-tetrahydroquinolin-3-yl)-amine, hydrochloride salt (277 mg, 0.92 mmol), prepared as described in Example 52A, and NaHCO$_3$ (773 mg, 9.2 mmol) in CH$_2$Cl$_2$ (10 mL) at RT was added phosgene (2.4 mL of 20% solution in toluene). After addition, the mixture was stirred at RT for 3 h and filtered. The filtrate was concentrated, the resultant residue dried in vacuo, then dissolved in toluene (5 mL) and treated with 1,4-cyclohexanediol (210 mg, 1.8 mmol). The mixture was stirred at 60° C. for 60 h, cooled to RT, and concentrated. The resultant residue was chromatographed (silica gel) eluting with EtOAc (0-25%) in hexanes to provide the title compound as a white solid (138 mg, 37%). HPLC (method B): 99% pure, retention time=6.76 min, MS (ES): m/z 406 [M+H]$^+$.

Example 53

[1-Benzyl-6-(2H-tetrazol-5-yl)-1,2,3,4-tetrahydroquinolin-3-yl]-carbamic acid cyclohexyl ester

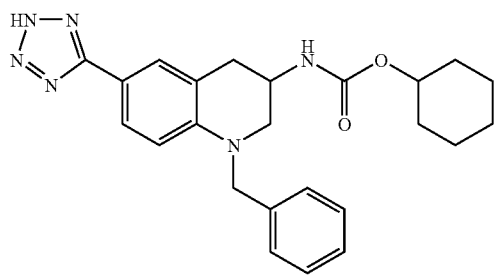

A solution of (1-benzyl-6-cyano-1,2,3,4-tetrahydroquinolin-3-yl)-carbamic acid cyclohexyl ester (195 mg, 0.5 mmol), prepared as described in Example 44, and azidotrimethylin (113.2 mg, 0.55 mmol) in toluene (3 mL) was refluxed under N$_2$ for 16 h. After cooling to RT, the reaction was concentrated. The residue was taken in MeOH (5 mL) and heated at 60° C. for 4 h, and then concentrated. The resulting residue was chromatographed (10 g silica gel) eluting with MeOH (0-5%) in EtOAc to give the title compound (120 mg, 56%) as a white solid. HPLC: (method B) 96% pure, retention time 7.8 min. MS (ES): m/z 433 [M+H]$^+$.

Example 54

[1-Benzyl-6-(2-methyl-2H-tetrazol-5-yl)-1,2,3,4-tetrahydroquinolin-3-yl]-carbamic acid cyclohexyl ester

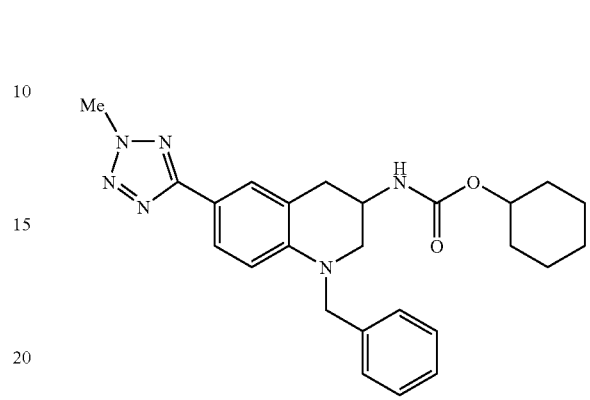

To a stirred solution of [1-benzyl-6-(2H-tetrazol-5-yl)-1,2,3,4-tetrahydroquinolin-3-yl]-carbamic acid cyclohexyl ester (61 mg, 0.14 mmol), prepared as described in Example 53, in CH$_3$CN (0.5 mL)-DMF (0.5 mL)-THF (0.5 mL) at RT was added Cs$_2$CO$_3$ (63.4 mg, 0.19 mmol), followed by iodomethane (7.8 µL, 0.126 mmol). The reaction mixture was stirred at RT for 16 h and then diluted with H$_2$O, extracted with EtOAc (10 mL×3). The organic extracts were washed saturated aqueous NaCl, dried Na$_2$SO$_4$), and concentrated. The resulting residue was purified using preparative HPLC [YMC S5 ODS (20×100 mm); Eluted with 50% to 90% B, 8 min gradient and 7 min hold. (A=90% H$_2$O-10% MeOH and B=10% H$_2$O-90% MeOH); Flow rate at 20 mL/min. UV detection at 220 nm] to give the title compound (regioisomer A, 35 mg, 56%) as a white solid. HPLC (method B): 98% pure, retention time=7.9 min. MS (ES): m/z 447 [M+H]$^+$.

Example 55

[1-Benzyl-6-(1-methyl-1H-tetrazol-5-yl)-1,2,3,4-tetrahydroquinolin-3-yl]-carbamic acid cyclohexyl ester

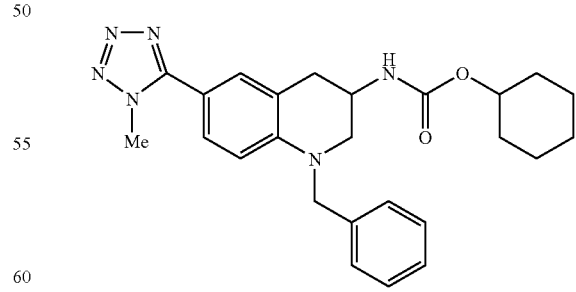

The title compound (regioisomer B) was separated from the crude mixture described in Example 54 using preparative HPLC (the same conditions as described in Example 54). HPLC (method B): 98% pure, retention time=7.4 min. MS (ES): m/z 447 [M+H]$^+$.

Biological Evaluation

Cannabinoid Receptor Binding Assay

Radioligand binding studies were conducted in membranes prepared from Chinese Hamster Ovary (CHO) cells that over-express recombinant human CB-1 (CHO-CB-1 cells). Total assay volume for the binding studies was 100 µl. 5 µg of membranes were brought up to a final volume of 95 µl with Binding Buffer (25 mM HEPES, 150 mM NaCl, 2.5 mM $CaCl_2$, 1 mM $MgCl_2$, 0.25% BSA). The diluted membranes were preincubated with a compound or DMSO vehicle. The binding reaction was initiated by the addition of 2 nM final $^3$H-CP-55,940 (120 Ci/mmol) and proceeded for 2.5 hours at room temperature. The binding reaction was terminated by transferring the reaction to GF/B 96 well plates (resoaked with 0.3% polyethylenimine) using a Packard Cell Harvester. The filter was washed with 0.25×PBS, 30 µl MicroScint was added per well, and the bound radiolabel was quantitated by scintillation counting on a Packard TopCount Scintillation Counter. The CB-2 radioligand binding assay was conducted identically except that the membranes from CHO-CB-2 cells were used.

For a compound to be considered a CB-1 antagonists the compound must possess a CB-1 receptor binding affinity Ki less than 13000 nM. As determined by the assay described above, the CB-1 receptor binding $K_i$ values of the working Examples fall within the range of 0.01 nM to 10000 nM.

Cannabinoid Receptor Functional Activity Assay

Functional CB-1 inverse agonist activity of test compounds was determined in CHO-CB-1 cells using a cAMP accumulation assay. CHO-CB-1 cells were grown in 96 well plates to near confluence. On the day of the functional assay, growth medium was aspirated and 100 of Assay Buffer (PBS plus 25 mM HEPES/0.1 mM 3-isobutyl-1-methylxanthine/ 0.1% BSA) was added. Compounds were added to the Assay buffer diluted 1:100 from 100% DMSO and allowed to pre-incubate for 10 minutes prior to addition of 5 uM forskolin. The mixture was allowed to proceed for 15 minutes at room temperature and was terminated by the addition of 0.1 N HCl. The total intracellular cAMP concentration was quantitated using the Amersham cAMP SPA kit.

Utilities and Combinations

Utilities

The compounds of the present invention are cannabinoid receptor modulators, and include compounds which are, for example, selective agonists, partial agonists, inverse agonists, antagonists or partial antagonists of the cannabinoid receptor. Accordingly, the compounds of the present invention may be useful for the treatment or prevention of diseases and disorders associated with G-protein coupled cannabinoid receptor activity. Preferably, compounds of the present invention possess activity as antagonists or inverse agonists of the CB-1 receptor, and may be used in the treatment of diseases or disorders associated with the activity of the CB-1 receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders) or psychiatric disorders, such as substance abuse, depression, anxiety, mania and schizophrenia. These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-induced hypotension). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

Compounds useful in the treatment of appetitive or motivational disorders regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a CB-1 receptor antagonist or inverse agonist for the treatment of bulimia and obesity, including obesity associated with type II diabetes (non-insulin-dependent diabetes), or more generally any disease resulting in the patient becoming overweight, Obesity, as described herein, is defined by a body mass index ($kg/m^2$) of at least 26. It may be due to any cause, whether genetic or environmental, including overeating and bulimia, polycystic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalants, nicotine, opioids, phencyclidine (or phencyclidine-like compounds), sedative-hypnotics or benzodiazepines, and other (or unknown) substances and combinations of the above. The terms "substance abuse disorders" also includes drug or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Dementias are diseases that include memory loss and additional intellectual impairment separate from memory. Cannabinoid receptor modulators may also be useful in treating cognitive impairments related to attentional deficits, such as attention deficit disorder.

Compounds in the present invention may also be useful in treating diseases associated with dysfunction of brain dopaminergic systems, such as Parkinson's Disease and substance abuse disorders. Parkinson's Disease is a neurodegenerative movement disorder characterized by bradykinesia and tremor.

As modulators of the cannabinoid receptor, the compounds of the present invention are further useful for the treatment and prevention of respiratory diseases and disorders. Respiratory diseases for which cannabinoid receptor modulators are useful include, but are not limited to, chronic pulmonary obstructive disorder, emphysema, asthma, and bronchitis. In addition, cannabinoid receptor modulators block the activation of lung epithelial cells by moieties such as allergic agents, inflammatory cytokines or smoke, thereby limiting release of mucin, cytokines, and chemokines, or selectively inhibiting lung epithelial cell activation.

Moreover, the compounds employed in the present invention may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present invention for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituitarism; Guillain-Barre syndrome; other autoimmune diseases; glomerulonephritis; serum sickness; urticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ischemia/reperfusion injury); dennatomyositis; alopecia greata; chronic actinic dermatitis; eczema; Behcet's disease; Pustulosis palmoplanteris; Pyoderma gangrenum; Sezary's syndrome; atopic dermatitis; systemic sclerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present invention inhibit the Fc gamma dependent production of TNF alpha in human monocytes/macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Further, cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present invention inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the cannabinoid receptor modulators in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio), a lipase inhibitor, such as orlistat or ATL-962 (Alizyme), serotonin receptor agonists, (e.g., BVT-933 (Biovitum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fabric acid derivatives), PPAR δ antagonists or agonists, PPARα/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), >-19702 (Sankyo/WL), N,N-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in, Yajima, K. et al., *Am. J. Physiol. Endocrinol. Metab.,* 284:E966-E971 (2003)), AZ-242 (tesaglitazar; Astra-Zeneca; as described in Ljung, B. et al., *J. Lipid Res.,* 43:1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of m-evalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31:1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Current Pharmaceutical Design*, 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog A and presqualene pyrophosphate (PSQ-PP) analogs as disclosed by Corey et al., *J. Am. Chem. Soc.*, 98:1291-1293 (1976), phosphinylphosphonates reported by McClard, R. W. et al., *J. Am. Chem. Soc.*, 109:5544 (1987) and cyclopropanes reported by Capson, T L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (TiHL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future*, 24:9-15 (1999) (Avasimibe); Nicolosi et al., "The ACAT inhibitor, C1-1011 is effective in the prevention and regression of aortic fatty streak area in hamsters", *Atherosclerosis* (Shannon, Irel.), 137(1):77-85 (1998); Ghiselli, G., "The pharmacological profile of FCE 27677: a novel ACAT inhibitor with potent hypolipidemic activity mediated by selective suppression of the hepatic secretion of ApoBf100-containing lipoprotein", *Cardiovasc. Drug Rev.*, 16(1):16-30 (1998); Smith, C. et al., "RP 73163; a bioavailable alkylsulfinyl-diphenylimidazole ACAT inhibitor", *Bioorg. Med. Chem. Lett.*, 6(1):47-50 (1996); Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways*, CRC Press, Inc., publ., Ruffolo, Jr., R. R. et al., eds., pp. 173-198 (1995); Sliskovic et al., "ACAT inhibitors: potential anti-atherosclerotic agents", *Curr. Med. Chem.*, 1(3):204-225 (1994); Stout et al., "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", *Chemtracts: Org. Chem.*, 8(6):359-362 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in Atherosclerosis, 115:45-63 (1995) and *J. Med. Chem.*, 41:973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacias SC-744 and SC-795, as well as CETi-1 and JTT-705.

The hypolipidemic agent may be an ileal Na$^+$/bile acid cotransporter inhibitor such as disclosed in *Drugs of the Future*, 24:425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g., diltiazem, verapamil, nifedipine, amlodipine and mybefradil), diuretics (e.g., chlorothiazide, hydroclhlorothiazide, flumethiazide, hydroflumethiazide, bendroflumethiazide, methylchlorothiazide, trichloromethiazide, polythiazide, benzthiazide, ethacrynic acid tricrynafen, chlorthalidone, firosemide, musolimine, bumetanide, triamtrenene, amiloride, spironolactoone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043, 265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Cannabinoid receptor modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

Cannabinoid receptor modulators may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

Cannabinoid receptor modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpha-adrenoreceptor antagonists, and atypical antidepressants (bupropion, lithium, nefazodone, trazodone and viloxazine).

The combination of a conventional antipsychotic drug with a CB-1 receptor antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), diphenylbutylpiperidine pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384, including TNF-alpha inhibitors, such as tenidap, anti-TNF antibodies or soluble TNF receptor such as etanercept (Enbrel®), rapamycin (sirolimus or Rapamune) and Jeflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-Ko openers such as those disclosed in U.S. Pat. No. 6,184,231 B1).

Exemplary of such other therapeutic agents which may be used in combination with cannabinoid receptor modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D. et al., "Cleavable CD40Ig Fusion Proteins and the Binding to Sgp39", *J. Immunol. Methods* (Netherlands), 188(1):1-7 (Dec. 15, 1995); Hollenbaugh, D. et al., "The Human T Cell Antigen Gp39, A Member of the TNF Gene Family, is a Ligand for the CD40 Receptor: Expression of a Soluble Form of Gp39 with B Cell Co-Stimulatory Activity", *EMBO J* (England), 11(12):4313-4321 (December 1992); and Moreland, L. W. et al., "Treatment of Rheumatoid Arthritis with a Recombinant Human Tumor Necrosis Factor Receptor (P75)-Fc Fusion Protein", *New Engl. J. Med.*, 337(3):141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of formula (I) of the invention can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably up to 100 mg in a regimen of single, two or four divided daily doses.

The compounds of the formula (I) can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A compound selected from the group consisting of:
    (S)-N-[1-(3-Chlorobenzyl)-6-cyano-1,2,3,4-tetrahydro-quinolin-3-yl]-2-cyclohexyl-acetamide;
    (S)-N-(6-Cyano-1-thiazol-5-ylmethyl-1,2,3,4-tetrahydro-quinolin-3-yl)benzamide;
    (R)-N-(6-Cyano-1-thiazol-5-ylmethyl-1,2,3,4-tetrahydro-quinolin-3-yl)benzamide;
    (S)-N-(1-Benzyl-6-cyano-1,2,3,4-tetrahydroquinolin-3 yl)-2-phenylacetamide;

(S)-N-(1-Benzyl-6-cyano-1,2,3,4-tetrahydroquinolin-3-yl)-2-cyclohexylacetamide;
(S)-N-(1-Benzyl-6-cyano-1,2,3,4-tetrahydroquinolin-3-yl)-3-cyclohexyl-propionamide;
N-(6-Cyano-1-phenethyl-1,2,3,4-tetrahydroquinolin-3-yl)-2-cyclohexylacetamide;
(S)-N-(1-Benzyl-6-cyano-1,2,3,4-tetrahydroquinolin-3-yl)-2-morpholin-4-yl-acetamide;
(R)-N-(1-Benzyl-6-cyano-1,2,3,4-tetrahydroquinolin-3-yl)-2-morpholin-4-yl-acetamide;
N-(6-Cyano-1-cyclohexyl-1,2,3,4-tetrahydroquinolin-3-yl)-2-cyclohexylacetamide;
N-(1-Benzyl-6-phenyl-1,2,3,4-tetrahydroquinolin-3-yl)-2-cyclohexylacetamide;
(S)-N-(1-Benzyl-6-bromo-1,2,3,4-tetrahydroquinolin-3-yl)-2-cyclohexylacetamide;
(R)-N-(1-Benzyl-6-bromo-1,2,3,4-tetrahydroquinolin-3-yl)-2-cyclohexylacetamide;
(S)-N-[1-(3-Chloro-benzyl)-6-cyano-1,2,3,4-tetrahydroquinolin-3-yl]-2-phenylacetamide;
(S)-N-(6-Cyano-1-pyridin-2-ylmethyl-1,2,3,4-tetrahydroquinolin-3-yl)-2-phenyl acetamide;
N-(1-benzyl-6-cyano-1,2,3,4-tetrahydroquinolin-3-yl)-2-methyl-2-(5-(trifluoromethyl)pyridin-2-yloxy)propanamide;
3-(Benzo[d][1,3]dioxol-5-yl)-N-(1-benzyl-6-chloro-1,2,3,4-tetrahydroquinolin-3-yl)propanamide;
N-(1-benzyl-6-chloro-1,2,3,4-tetrahydroquinolin-3-yl)-2-(benzyloxy)propanamide;
N-(1-benzyl-6-chloro-1,2,3,4-tetrahydroquinolin-3-yl)-2-(2-methoxyphenyl)acetamide;
N-(1-benzyl-6-chloro-1,2,3,4-tetrahydroquinolin-3-yl)-3-(3-methoxyphenyl)propanamide;
N-(1-benzyl-6-chloro-1,2,3,4-tetrahydroquinolin-3-yl)-2-(3,5-dimethoxyphenyl)acetamide;
3-(benzo[d][1,3]dioxol-5-yl)-N-(1-benzyl-6-chloro-1,2,3,4-tetrahydroquinolin-3-yl)propanamide;
N-(1-benzyl-6-chloro-1,2,3,4-tetrahydroquinolin-3-yl)-2-(1,3-dioxoisoindolin-2-yl)propanamide;
tert-butyl 2-((1-benzyl-6-chloro-1,2,3,4-tetrahydroquinolin-3-yl)carbamoyl)benzoate;
N-(1-benzyl-6-chloro-1,2,3,4-tetrahydroquinolin-3-yl)-2-(1H-pyrrol-1-yl)benzamide;
(2R)-N-(1-Benzyl-6-(4-fluorophenyl)-1,2,3,4-tetrahydroquinolin-3-yl)-2-hydroxy-3-phenylpropanamide;
(2S)-N-(1-Benzyl-6-(4-fluorophenyl)-1,2,3,4-tetrahydroquinolin-3-yl)-2-hydroxy-3-phenylpropanamide;
(2S)-N-(1-benzyl-6-(4-fluorophenyl)-1,2,3,4-tetrahydroquinolin-3-yl)-2-hydroxy-4-phenylbutanamide;
N-(1-benzyl-6-(4-fluorophenyl)-1,2,3,4-tetrahydroquinolin-3-yl)-2-hydroxy-3-(1H-indol-2-yl)propanamide;
N-(1-benzyl-6-(4-fluorophenyl)-1,2,3,4-tetrahydroquinolin-3-yl)-3-(2-methoxyphenyl)propanamide;
N-(1-benzyl-6-(4-fluorophenyl)-1,2,3,4-tetrahydroquinolin-3-yl)-3-(3-methoxyphenyl)propanamide;
N-(1-benzyl-6-(4-fluorophenyl)-1,2,3,4-tetrahydroquinolin-3-yl)-3-(4-methoxyphenyl)propanamide;
N-(1-benzyl-6-(4-fluorophenyl)-1,2,3,4-tetrahydroquinolin-3-yl)-3-(2-hydroxyphenyl)propanamide;
N-(1-benzyl-6-(4-fluorophenyl)-1,2,3,4-tetrahydroquinolin-3-yl)-3-(3-hydroxyphenyl)propanamide;
N-(1-benzyl-6-(4-fluorophenyl)-1,2,3,4-tetrahydroquinolin-3-yl)-3-(4-hydroxyphenyl)propanamide;
N-(1-benzyl-6-(4-fluorophenyl)-1,2,3,4-tetrahydroquinolin-3-yl)-3-phenylpropanamide;
N-(1-benzyl-6-(4-fluorophenyl)-1,2,3,4-tetrahydroquinolin-3-yl)-2-methyl-2-(5-(trifluoromethyl)pyridin-2-yloxy)propanamide;
(S)-1-[1-(3-Chloro-benzyl)-6-cyano-1,2,3,4-tetrahydroquinolin-3-yl]-3-cyclohexylurea;
(S)-[1-(3-Chlorobenzyl)-6-cyano-1,2,3,4-tetrahydroquinolin-3-yl]-carbamic acid cyclohexyl ester;
(S)-[1-(3-Chlorobenzyl)-6-cyano-1,2,3,4-tetrahydroquinolin-3-yl]-carbamic acid cyclohexyl ester;
(R)-[1-(3-Chlorobenzyl)-6-cyano-1,2,3,4-tetrahydroquinolin-3-yl]-carbamic acid cyclohexyl ester;
(1-Benzyl-6-cyano-1,2,3,4-tetrahydroquinolin-3-yl)-carbamic acid cyclohexyl ester;
(S)-(1-Benzyl-6-cyano-1,2,3,4-tetrahydroquinolin-3-yl)-carbamic acid cyclohexyl ester;
(R)-(1-Benzyl-6-cyano-1,2,3,4-tetrahydroquinolin-3-yl)-carbamic acid cyclohexyl ester;
(S)-(1-Benzyl-6-cyano-1,2,3,4-tetrahydroquinolin-3-yl)-carbamic acid benzyl ester;
(R)-(1-Benzyl-6-cyano-1,2,3,4-tetrahydroquinolin-3-yl)-carbamic acid benzyl ester;
(S)-(1-Benzyl-6-cyano-1,2,3,4-tetrahydroquinolin-3-yl)-carbamic acid tetrahydro-pyran-4-yl ester;
(6-Cyano-1-phenethyl-1,2,3,4-tetrahydroquinolin-3-yl)-carbamic acid cyclohexyl ester;
(1-Benzyl-6-bromo-1,2,3,4-tetrahydroquinolin-3-yl)-carbamic acid cyclohexyl ester;
(1-Benzyl-6-cyano-1,2,3,4-tetrahydroquinolin-3-yl)-carbamic acid 4-hydroxy-cyclohexyl ester;
[1-Benzyl-6-(2H-tetrazol-5-yl)-1,2,3,4-tetrahydroquinolin-3-yl]-carbamic acid cyclohexyl ester;
[1-Benzyl-6-(2-methyl-2H-tetrazol-5-yl)-1,2,3,4-tetrahydroquinolin-3-yl]-carbamic acid cyclohexyl ester; and
[1-Benzyl-6-(1-methyl-1H-tetrazol-5-yl)-1,2,3,4-tetrahydroquinolin-3-yl]-carbamic acid cyclohexyl ester.

2. A pharmaceutical composition comprising at least compound according to claim 1 and at least one pharmaceutically acceptable diluent or carrier.

\* \* \* \* \*